US011039816B2

(12) United States Patent
McWeeney et al.

(10) Patent No.: US 11,039,816 B2
(45) Date of Patent: Jun. 22, 2021

(54) NEEDLE BIOPSY DEVICE WITH EXCHANGEABLE NEEDLE AND INTEGRATED NEEDLE PROTECTION

(71) Applicant: COVIDIEN LP, Mansfield, MA (US)

(72) Inventors: John O. McWeeney, Brighton, MA (US); Michael E. Kelly, Clare (IE)

(73) Assignee: Covidien LP, Mansfield, MA (US)

( * ) Notice: Subject to any disclaimer, the term of this patent is extended or adjusted under 35 U.S.C. 154(b) by 187 days.

(21) Appl. No.: 15/084,851

(22) Filed: Mar. 30, 2016

(65) Prior Publication Data
US 2016/0206294 A1     Jul. 21, 2016

Related U.S. Application Data

(63) Continuation of application No. 13/297,766, filed on Nov. 16, 2011, now Pat. No. 9,332,973, which is a
(Continued)

(51) Int. Cl.
*A61B 10/02*     (2006.01)
*A61B 10/04*     (2006.01)
(Continued)

(52) U.S. Cl.
CPC ...... *A61B 10/0233* (2013.01); *A61B 10/0283* (2013.01); *A61B 10/04* (2013.01);
(Continued)

(58) Field of Classification Search
CPC ......... A61B 10/00; A61B 10/02; A61B 10/06; A61B 2010/0208; A61B 2010/0233; A61B 2010/045; A61B 17/34; A61B 17/3478
See application file for complete search history.

(56) References Cited

U.S. PATENT DOCUMENTS 3,612,050 A   10/1971  Sheridan
3,666,808 A    5/1972  Meek
(Continued)

FOREIGN PATENT DOCUMENTS

EP     0704189 A1    4/1996
EP     0738501 A1   10/1996
(Continued)

OTHER PUBLICATIONS

Patent Examination Report No. 1 for Patent Application No. 2012339659, dated Sep. 22, 2016, from Australian Government IP Australia.
(Continued)

*Primary Examiner* — Rene T Towa
(74) *Attorney, Agent, or Firm* — Holland & Hart LLP

(57) ABSTRACT

The invention provides device for needle biopsy having a novel delivery handle system for interchangeably delivering needles of various sizes to a biopsy site. The delivery handle system is adjustable in length and includes a proximal slideably disposed over a middle handle member, the middle handle member is slideably disposed over a distal handle member. The proximal handle member includes an inner hub housing component configured to interchangeably receive a needle subassembly that can be inserting into and withdrawn from the proximal handle member. The needle subassembly includes a needle of a plurality of different sizes, a needle luer, a needle hub coupled to a proximal end portion of the needle, and a needle protector subassembly. The needle protector subassembly includes a needle protection hub configured to receive the distal end of a needle.

20 Claims, 23 Drawing Sheets

Related U.S. Application Data continuation-in-part of application No. 13/029,593, filed on Feb. 17, 2011, now abandoned, and a continuation-in-part of application No. 12/607,636, filed on Oct. 28, 2009, now Pat. No. 8,968,210, and a continuation-in-part of application No. 12/243,367, filed on Oct. 1, 2008, now Pat. No. 9,186,128.

(60) Provisional application No. 61/305,304, filed on Feb. 17, 2010, provisional application No. 61/305,396, filed on Feb. 17, 2010, provisional application No. 61/117,966, filed on Nov. 26, 2008, provisional application No. 61/152,741, filed on Feb. 16, 2009.

(51) Int. Cl.
    *A61B 90/00*     (2016.01)
    *A61B 17/00*     (2006.01)
    *A61B 17/34*     (2006.01)

(52) U.S. Cl.
    CPC ............... *A61B 2010/045* (2013.01); *A61B 2017/00469* (2013.01); *A61B 2017/00477* (2013.01); *A61B 2017/00991* (2013.01); *A61B 2017/3413* (2013.01); *A61B 2090/0801* (2016.02); *A61B 2090/3925* (2016.02)

(56) References Cited

U.S. PATENT DOCUMENTS

| | | | |
|---|---|---|---|
| 4,160,450 A * | 7/1979 | Doherty | A61M 25/0606 604/162 |
| 4,249,541 A | 2/1981 | Pratt | |
| 4,356,828 A | 11/1982 | Jamshidi | |
| 4,467,816 A | 8/1984 | Schluter et al. | |
| 4,655,226 A | 4/1987 | Lee | |
| 4,819,637 A | 4/1989 | Dormandy, Jr. et al. | |
| 4,838,280 A | 6/1989 | Haaga | |
| 4,857,057 A * | 8/1989 | Sanagi | A61B 1/015 604/170.01 |
| 4,861,341 A | 8/1989 | Woodburn | |
| 4,893,635 A | 1/1990 | de Groot et al. | |
| 4,903,523 A | 2/1990 | Flynn | |
| 4,966,162 A | 10/1990 | Wang | |
| 4,995,866 A | 2/1991 | Amplatz et al. | |
| 5,054,310 A | 10/1991 | Flynn | |
| 5,057,085 A | 10/1991 | Kopans | |
| 5,111,829 A | 5/1992 | Alvarez de Toledo | |
| 5,131,393 A | 7/1992 | Ishiguro et al. | |
| 5,215,528 A | 6/1993 | Purdy et al. | |
| 5,257,628 A | 11/1993 | Ishiguro et al. | |
| 5,266,359 A | 11/1993 | Spielvogel | |
| 5,277,199 A | 1/1994 | DuBois et al. | |
| 5,281,408 A | 1/1994 | Unger | |
| 5,300,045 A * | 4/1994 | Plassche, Jr. | A61M 5/3273 604/158 |
| 5,333,613 A | 8/1994 | Tickner et al. | |
| 5,368,036 A | 11/1994 | Tanaka et al. | |
| 5,376,075 A * | 12/1994 | Haughton | A61M 5/158 604/158 |
| 5,380,292 A | 1/1995 | Wilson | |
| 5,419,310 A | 5/1995 | Frassica et al. | |
| 5,458,112 A | 10/1995 | Weaver | |
| 5,470,308 A | 11/1995 | Edwards et al. | |
| 5,471,988 A | 12/1995 | Fujio et al. | |
| 5,480,389 A | 1/1996 | McWha et al. | |
| 5,490,521 A | 2/1996 | Davis et al. | |
| 5,526,822 A | 6/1996 | Burbank et al. | |
| 5,595,724 A | 1/1997 | Deutsch et al. | |
| 5,601,588 A | 2/1997 | Tonomura et al. | |
| 5,607,389 A | 3/1997 | Edwards et al. | |
| 5,609,850 A | 3/1997 | Deutsch et al. | |
| 5,636,255 A | 6/1997 | Ellis | |
| 5,681,348 A | 10/1997 | Sato | |
| 5,688,490 A | 11/1997 | Tournier et al. | |
| 5,695,491 A | 12/1997 | Silverstein | |
| 5,775,333 A | 7/1998 | Burbank et al. | |
| 5,800,445 A | 9/1998 | Ratcliff et al. | |
| 5,810,806 A | 9/1998 | Ritchart et al. | |
| 5,820,609 A * | 10/1998 | Saito | 604/272 |
| 5,848,978 A | 12/1998 | Cecchi | |
| 5,888,201 A | 3/1999 | Stinson et al. | |
| 5,902,310 A | 5/1999 | Foerster et al. | |
| 5,919,172 A | 7/1999 | Golba, Jr. | |
| 5,921,933 A | 7/1999 | Sarkis et al. | |
| 5,928,164 A | 7/1999 | Burbank et al. | |
| 5,938,635 A | 8/1999 | Khule | |
| 5,941,890 A | 8/1999 | Voegele et al. | |
| 5,944,673 A | 8/1999 | Gregoire et al. | |
| 5,947,964 A | 9/1999 | Eggers et al. | |
| 5,964,740 A * | 10/1999 | Ouchi | 604/264 |
| 5,967,988 A | 10/1999 | Briscoe et al. | |
| 5,968,022 A | 10/1999 | Saito | |
| 5,980,469 A | 11/1999 | Burbank et al. | |
| 6,019,733 A | 2/2000 | Farasconi | |
| 6,045,497 A | 4/2000 | Schweich, Jr. et al. | |
| 6,077,248 A * | 6/2000 | Zumschlinge | A61B 17/3415 604/167.01 |
| 6,080,115 A | 6/2000 | Rubinstein | |
| 6,106,473 A | 8/2000 | Violante et al. | |
| 6,106,524 A | 8/2000 | Eggers et al. | |
| 6,117,108 A | 9/2000 | Woehr et al. | |
| 6,126,633 A * | 10/2000 | Kaji et al. | 604/95.04 |
| 6,133,316 A | 10/2000 | Ostensen et al. | |
| 6,149,598 A | 11/2000 | Tanaka | |
| 6,161,034 A | 12/2000 | Burbank et al. | |
| 6,168,779 B1 | 1/2001 | Barsky et al. | |
| 6,171,249 B1 | 1/2001 | Chin et al. | |
| 6,174,291 B1 | 1/2001 | McMahon et al. | |
| 6,179,809 B1 | 1/2001 | Khairkhahan et al. | |
| 6,193,692 B1 | 2/2001 | Harris et al. | |
| 6,221,622 B1 | 4/2001 | Love | |
| 6,228,039 B1 | 5/2001 | Binmoeller | |
| 6,228,049 B1 | 5/2001 | Schroeder et al. | |
| 6,231,515 B1 | 5/2001 | Moore et al. | |
| 6,261,302 B1 | 7/2001 | Voegele et al. | |
| 6,273,861 B1 | 8/2001 | Bates et al. | |
| 6,280,399 B1 | 8/2001 | Rossin et al. | |
| 6,287,304 B1 | 9/2001 | Eggers et al. | |
| 6,312,428 B1 | 11/2001 | Eggers et al. | |
| 6,323,335 B1 | 11/2001 | Huang | |
| 6,328,701 B1 | 12/2001 | Terwilliger | |
| 6,333,155 B1 | 12/2001 | Lockhart et al. | |
| 6,334,067 B1 | 12/2001 | Brabrand | |
| 6,336,812 B1 | 1/2002 | Cooper et al. | |
| 6,337,994 B1 | 1/2002 | Stoianovici et al. | |
| 6,338,968 B1 | 1/2002 | Hefti | |
| 6,340,563 B1 | 1/2002 | Finkelstein et al. | |
| 6,340,565 B1 | 1/2002 | Oliner et al. | |
| 6,340,568 B2 | 1/2002 | Hefti | |
| 6,344,316 B1 | 2/2002 | Lockhart et al. | |
| 6,344,317 B2 | 2/2002 | Urnovitz | |
| 6,347,240 B1 | 2/2002 | Foley et al. | |
| 6,347,241 B2 | 2/2002 | Burbank et al. | |
| 6,350,244 B1 | 2/2002 | Fisher | |
| 6,350,274 B1 | 2/2002 | Li | |
| 6,350,583 B1 | 2/2002 | Cohen et al. | |
| 6,351,660 B1 | 2/2002 | Burke et al. | |
| 6,355,033 B1 | 3/2002 | Moorman et al. | |
| 6,355,275 B1 | 3/2002 | Klein | |
| 6,355,424 B1 | 3/2002 | Lorincz et al. | |
| 6,356,782 B1 | 3/2002 | Sirimanne et al. | |
| 6,361,499 B1 | 3/2002 | Bates et al. | |
| 6,361,948 B1 | 3/2002 | Tricoli et al. | |
| 6,364,526 B2 | 4/2002 | Ivan et al. | |
| 6,365,362 B1 | 4/2002 | Terstappen et al. | |
| 6,365,712 B1 | 4/2002 | Kelly | |
| 6,368,280 B1 | 4/2002 | Cermak et al. | |
| 6,368,292 B1 | 4/2002 | Ogden et al. | |
| 6,368,792 B1 | 4/2002 | Billing-Medel et al. | |
| 6,368,795 B1 | 4/2002 | Hefti | |
| 6,368,799 B1 | 4/2002 | Chee | |
| 6,369,195 B1 | 4/2002 | An et al. | |

(56) References Cited

U.S. PATENT DOCUMENTS

| | | |
|---|---|---|
| 6,371,904 B1 | 4/2002 | Sirimanne et al. |
| 6,371,917 B1 | 4/2002 | Ferrara et al. |
| 6,372,431 B1 | 4/2002 | Cunningham et al. |
| 6,372,444 B1 | 4/2002 | Powers et al. |
| 6,374,135 B1 | 4/2002 | Bucholz |
| 6,375,634 B1 | 4/2002 | Carroll |
| 6,375,953 B1 | 4/2002 | Srivastava et al. |
| 6,376,258 B2 | 4/2002 | Hefti |
| 6,379,671 B1 | 4/2002 | Colpitts |
| 6,379,672 B1 | 4/2002 | Srivastava et al. |
| 6,383,484 B1 | 5/2002 | Achen et al. |
| 6,383,491 B1 | 5/2002 | Srivastava et al. |
| 6,383,492 B1 | 5/2002 | Srivastava et al. |
| 6,383,493 B1 | 5/2002 | Srivastava et al. |
| 6,387,056 B1 | 5/2002 | Kieturakis |
| 6,387,374 B1 | 5/2002 | Srivastava et al. |
| 6,387,629 B1 | 5/2002 | Schneider et al. |
| 6,391,306 B1 | 5/2002 | Srivastava et al. |
| 6,391,542 B1 | 5/2002 | Anderson et al. |
| 6,391,543 B2 | 5/2002 | Billing-Medel et al. |
| 6,394,965 B1 | 5/2002 | Klein |
| 6,395,480 B1 | 5/2002 | Hefti |
| 6,398,737 B2 | 6/2002 | Moore et al. |
| 6,399,069 B1 | 6/2002 | Srivastava et al. |
| 6,399,070 B1 | 6/2002 | Srivastava et al. |
| 6,399,371 B1 | 6/2002 | Falduto et al. |
| 6,402,701 B1 | 6/2002 | Kaplan et al. |
| 6,403,095 B1 | 6/2002 | Srivastava et al. |
| 6,405,733 B1 | 6/2002 | Fogarty et al. |
| 6,407,125 B1 | 6/2002 | Fernandez-Pol |
| 6,409,664 B1 | 6/2002 | Kattan et al. |
| 6,410,028 B1 | 6/2002 | Srivastava |
| 6,410,229 B1 | 6/2002 | Lockhart et al. |
| 6,413,751 B1 | 7/2002 | Benkovic et al. |
| 6,416,484 B1 | 7/2002 | Miller et al. |
| 6,421,559 B1 | 7/2002 | Pearlman |
| 6,423,081 B1 | 7/2002 | Lee et al. |
| 6,423,313 B1 | 7/2002 | Esmon et al. |
| 6,423,489 B1 | 7/2002 | Anderson et al. |
| 6,423,494 B1 | 7/2002 | Jin et al. |
| 6,423,503 B1 | 7/2002 | Mikolajczyk et al. |
| 6,426,195 B1 | 7/2002 | Zhong et al. |
| 6,426,367 B1 | 7/2002 | Das |
| 6,427,081 B1 | 7/2002 | Burbank et al. |
| 6,427,089 B1 | 7/2002 | Knowlton |
| 6,428,463 B1 | 8/2002 | Ravins et al. |
| 6,428,479 B1 | 8/2002 | Aksnes et al. |
| 6,428,487 B1 | 8/2002 | Burdorff et al. |
| 6,432,035 B1 | 8/2002 | Ravins et al. |
| 6,432,053 B1 | 8/2002 | Fecht et al. |
| 6,432,065 B1 | 8/2002 | Burdorff et al. |
| 6,432,700 B1 | 8/2002 | Henderson et al. |
| 6,434,415 B1 | 8/2002 | Foley et al. |
| 6,436,054 B1 | 8/2002 | Viola et al. |
| 6,436,120 B1 | 8/2002 | Meglin |
| 6,436,394 B1 | 8/2002 | Henderson et al. |
| 6,436,404 B1 | 8/2002 | Srivastava et al. |
| 6,436,411 B1 | 8/2002 | Riordan et al. |
| 6,440,086 B1 | 8/2002 | Hohenberg |
| 6,440,147 B1 | 8/2002 | Lee et al. |
| 6,440,151 B1 | 8/2002 | Cragg et al. |
| 6,440,153 B2 | 8/2002 | Cragg et al. |
| 6,443,960 B1 | 9/2002 | Brabrand et al. |
| 6,445,767 B1 | 9/2002 | Karellas |
| 6,447,477 B2 | 9/2002 | Burney et al. |
| 6,447,534 B2 | 9/2002 | Cragg et al. |
| 6,447,780 B1 | 9/2002 | Srivastava et al. |
| 6,447,781 B1 | 9/2002 | Srivastava |
| 6,447,997 B1 | 9/2002 | Los et al. |
| 6,448,020 B1 | 9/2002 | Toftgard et al. |
| 6,450,973 B1 | 9/2002 | Murphy |
| 6,455,027 B1 | 9/2002 | Barsky et al. |
| 6,455,048 B1 | 9/2002 | Srivastava et al. |
| 6,455,251 B1 | 9/2002 | Waldman |
| 6,459,925 B1 | 10/2002 | Nields et al. |
| 6,461,615 B1 | 10/2002 | Srivastava |
| 6,463,319 B1 | 10/2002 | Bucholz |
| 6,464,648 B1 | 10/2002 | Nakamura |
| 6,465,181 B2 | 10/2002 | Billing-Medel et al. |
| 6,465,183 B2 | 10/2002 | Wolber |
| 6,468,985 B1 | 10/2002 | Huang |
| 6,470,217 B1 | 10/2002 | Fenn et al. |
| 6,471,659 B2 | 10/2002 | Eggers et al. |
| 6,471,678 B1 * | 10/2002 | Alvarez de Toledo ...................... A61B 17/3478 600/104 |
| 6,471,700 B1 | 10/2002 | Burbank et al. |
| 6,471,709 B1 | 10/2002 | Fawzi et al. |
| 6,472,518 B1 | 10/2002 | Ribot et al. |
| 6,475,732 B1 | 11/2002 | Shayesteh et al. |
| 6,475,789 B1 | 11/2002 | Cech et al. |
| 6,477,426 B1 | 11/2002 | Fenn et al. |
| 6,482,182 B1 | 11/2002 | Carroll et al. |
| 6,482,599 B1 | 11/2002 | Mikolajczyk et al. |
| 6,485,308 B1 | 11/2002 | Goldstein |
| 6,485,436 B1 | 11/2002 | Truckai et al. |
| 6,485,905 B2 | 11/2002 | Hefti |
| 6,488,636 B2 | 12/2002 | Bryan et al. |
| 6,489,097 B2 | 12/2002 | Hirose et al. |
| 6,489,113 B1 | 12/2002 | Traish |
| 6,490,467 B1 | 12/2002 | Bucholz et al. |
| 6,491,699 B1 | 12/2002 | Henderson et al. |
| 6,491,702 B2 | 12/2002 | Heilbrun et al. |
| 6,492,115 B1 | 12/2002 | Guida et al. |
| 6,494,844 B1 | 12/2002 | Van Bladel et al. |
| 6,494,859 B2 | 12/2002 | Love et al. |
| 6,494,879 B2 | 12/2002 | Lennox et al. |
| 6,495,130 B1 | 12/2002 | Henderson et al. |
| 6,496,717 B2 | 12/2002 | Cox et al. |
| 6,497,706 B1 | 12/2002 | Burbank et al. |
| 6,500,622 B2 | 12/2002 | Bruchez, Jr. et al. |
| 6,500,938 B1 | 12/2002 | Au-Young et al. |
| 6,505,125 B1 | 1/2003 | Ho |
| 6,506,156 B1 | 1/2003 | Jones et al. |
| 6,506,607 B1 | 1/2003 | Shyjan |
| 6,507,748 B2 | 1/2003 | Selland |
| 6,508,755 B1 | 1/2003 | Ravins et al. |
| 6,508,789 B1 | 1/2003 | Sinnott et al. |
| 6,509,458 B1 | 1/2003 | Afar et al. |
| 6,509,514 B1 | 1/2003 | Kneteman et al. |
| 6,514,248 B1 | 2/2003 | Eggers et al. |
| 6,514,251 B1 | 2/2003 | Ni et al. |
| 6,514,685 B1 | 2/2003 | Moro |
| 6,514,695 B1 | 2/2003 | Barsky et al. |
| 6,517,498 B1 | 2/2003 | Burbank et al. |
| 6,521,211 B1 | 2/2003 | Unger et al. |
| 6,524,800 B2 | 2/2003 | Lockhart et al. |
| 6,527,731 B2 | 3/2003 | Weiss et al. |
| 6,530,888 B2 | 3/2003 | Smith et al. |
| 6,535,756 B1 | 3/2003 | Simon et al. |
| 6,537,761 B2 | 3/2003 | Shayesteh et al. |
| 6,538,119 B2 | 3/2003 | Billing-Medel et al. |
| 6,540,694 B1 | 4/2003 | Van Bladel et al. |
| 6,540,695 B1 | 4/2003 | Burbank et al. |
| 6,544,236 B1 | 4/2003 | Cragg et al. |
| 6,544,544 B2 | 4/2003 | Hunter et al. |
| 6,546,787 B1 | 4/2003 | Schiller et al. |
| 6,548,257 B2 | 4/2003 | Lockhart et al. |
| 6,551,255 B2 | 4/2003 | Van Bladel et al. |
| 6,551,784 B2 | 4/2003 | Fodor et al. |
| 6,552,164 B1 | 4/2003 | Colpitts et al. |
| 6,552,181 B1 | 4/2003 | Dean et al. |
| 6,554,779 B2 | 4/2003 | Viola et al. |
| 6,558,407 B1 | 5/2003 | Ivanko et al. |
| 6,558,916 B2 | 5/2003 | Veerapandian et al. |
| 6,562,562 B2 | 5/2003 | Casu' et al. |
| 6,564,087 B1 | 5/2003 | Pitris et al. |
| 6,564,806 B1 | 5/2003 | Fogarty et al. |
| 6,566,078 B1 | 5/2003 | Raitano et al. |
| 6,566,079 B2 | 5/2003 | Hefti |
| 6,567,214 B2 | 5/2003 | Lorincz |
| 6,567,689 B2 | 5/2003 | Burbank et al. |
| 6,568,941 B1 | 5/2003 | Goldstein |
| 6,572,551 B1 | 6/2003 | Smith et al. |

(56) References Cited

U.S. PATENT DOCUMENTS

| | | |
|---|---|---|
| 6,572,578 B1 | 6/2003 | Blanchard |
| 6,577,904 B1 | 6/2003 | Zhang et al. |
| 6,579,891 B1 | 6/2003 | Fernandez-Pol |
| 6,580,938 B1 | 6/2003 | Acker |
| 6,582,368 B2 | 6/2003 | Holdaway et al. |
| 6,582,426 B2 | 6/2003 | Moorman et al. |
| 6,585,968 B2 | 7/2003 | Little et al. |
| 6,586,713 B2 | 7/2003 | Essenfeld et al. |
| 6,587,578 B2 | 7/2003 | Godik et al. |
| 6,589,240 B2 | 7/2003 | Hinchliffe |
| 6,592,508 B1 | 7/2003 | Ravins et al. |
| 6,592,530 B1 | 7/2003 | Farhadi |
| 6,599,247 B1 | 7/2003 | Stetten |
| 6,602,659 B1 | 8/2003 | Waldman et al. |
| 6,604,404 B2 | 8/2003 | Paltieli et al. |
| 6,605,294 B2 | 8/2003 | Sawhney |
| 6,607,561 B2 | 8/2003 | Brannon |
| 6,608,191 B1 | 8/2003 | Anderson et al. |
| 6,608,310 B2 | 8/2003 | Soluri et al. |
| 6,610,016 B1 | 8/2003 | Violante et al. |
| 6,610,499 B1 | 8/2003 | Fulwyler et al. |
| 6,610,839 B1 | 8/2003 | Morin et al. |
| 6,612,991 B2 | 9/2003 | Sauer et al. |
| 6,613,740 B1 | 9/2003 | Gozes et al. |
| 6,614,921 B1 | 9/2003 | Chung et al. |
| 6,617,110 B1 | 9/2003 | Chech et al. |
| 6,617,137 B2 | 9/2003 | Dean et al. |
| 6,623,437 B2 | 9/2003 | Hinchliffe et al. |
| 6,626,832 B1 | 9/2003 | Paltieli et al. |
| 6,626,848 B2 | 9/2003 | Neuenfeldt |
| 6,626,850 B1 | 9/2003 | Chau et al. |
| 6,626,903 B2 | 9/2003 | McGuckin, Jr. et al. |
| 6,626,930 B1 | 9/2003 | Allen et al. |
| 6,627,414 B2 | 9/2003 | Billing-Medel et al. |
| 6,627,461 B2 | 9/2003 | Chapman et al. |
| 6,629,959 B2 | 10/2003 | Kuracina et al. |
| 6,631,204 B1 | 10/2003 | Smith |
| 6,632,183 B2 | 10/2003 | Bowman et al. |
| 6,638,234 B2 | 10/2003 | Burbank et al. |
| 6,638,719 B1 | 10/2003 | Gunderson et al. |
| 6,638,727 B1 | 10/2003 | Hung et al. |
| 6,645,731 B2 | 11/2003 | Terstappen et al. |
| 6,647,285 B2 | 11/2003 | Da Silva et al. |
| 6,649,420 B1 | 11/2003 | Cantor |
| 6,652,520 B2 | 11/2003 | Moorman et al. |
| 6,652,859 B1 | 11/2003 | Afar et al. |
| 6,653,080 B2 | 11/2003 | Bruchez et al. |
| 6,653,129 B1 | 11/2003 | Bander et al. |
| 6,654,120 B2 | 11/2003 | Ban |
| 6,654,629 B2 | 11/2003 | Montegrande |
| 6,656,132 B1 | 12/2003 | Ouchi |
| 6,659,105 B2 | 12/2003 | Burbank et al. |
| 6,660,834 B2 | 12/2003 | Billing-Medel et al. |
| 6,662,041 B2 | 12/2003 | Burbank et al. |
| 6,663,560 B2 | 12/2003 | MacAulay et al. |
| 6,666,811 B1 | 12/2003 | Good |
| 6,670,122 B2 | 12/2003 | Rosenow et al. |
| 6,673,023 B2 | 1/2004 | Pflueger |
| 6,673,914 B1 | 1/2004 | Hoon |
| 6,675,037 B1 | 1/2004 | Tsekos |
| 6,676,610 B2 | 1/2004 | Morton et al. |
| 6,676,658 B2 | 1/2004 | Burbank et al. |
| 6,676,935 B2 | 1/2004 | Henderson et al. |
| 6,676,984 B1 | 1/2004 | Sharp et al. |
| 6,677,157 B1 | 1/2004 | Cohen |
| 6,678,545 B2 | 1/2004 | Bucholz |
| 6,678,552 B2 | 1/2004 | Pearlman |
| 6,679,851 B2 | 1/2004 | Burbank et al. |
| 6,680,178 B2 | 1/2004 | Harris et al. |
| 6,689,062 B1 | 2/2004 | Mesallum |
| 6,689,065 B2 | 2/2004 | Aksnes et al. |
| 6,689,067 B2 | 2/2004 | Sauer et al. |
| 6,689,071 B2 | 2/2004 | Burbank et al. |
| 6,689,072 B2 | 2/2004 | Kaplan et al. |
| 6,689,073 B2 | 2/2004 | Quay |
| 6,689,744 B2 | 2/2004 | Gao et al. |
| 6,689,787 B1 | 2/2004 | McKeam et al. |
| 6,690,371 B1 | 2/2004 | Okerlund et al. |
| 6,690,966 B1 | 2/2004 | Rava et al. |
| 6,690,976 B2 | 2/2004 | Fenn et al. |
| 6,692,467 B2 | 2/2004 | McFarlane |
| 6,692,724 B1 | 2/2004 | Yang et al. |
| 6,692,736 B2 | 2/2004 | Yu et al. |
| 6,695,779 B2 | 2/2004 | Sauer et al. |
| 6,697,665 B1 | 2/2004 | Rava et al. |
| 6,699,205 B2 | 3/2004 | Fulton, III et al. |
| 6,702,749 B2 | 3/2004 | Paladini et al. |
| 6,702,761 B1 | 3/2004 | Damadian et al. |
| 6,702,831 B2 | 3/2004 | Lee et al. |
| 6,703,216 B2 | 3/2004 | Parsons et al. |
| 6,705,994 B2 | 3/2004 | Vortman et al. |
| 6,709,408 B2 | 3/2004 | Fisher |
| 6,709,816 B1 | 3/2004 | Huang et al. |
| 6,712,773 B1 | 3/2004 | Viola |
| 6,712,785 B2 | 3/2004 | Morton et al. |
| 6,714,808 B2 | 3/2004 | Klimberg et al. |
| 6,716,179 B2 | 4/2004 | Burbank et al. |
| 6,722,371 B1 | 4/2004 | Fogarty et al. |
| 6,723,052 B2 | 4/2004 | Mills |
| 6,723,106 B1 | 4/2004 | Charles et al. |
| 6,723,498 B1 | 4/2004 | Shyjan et al. |
| 6,725,080 B2 | 4/2004 | Melkent et al. |
| 6,725,083 B1 | 4/2004 | Burbank et al. |
| 6,725,095 B2 | 4/2004 | Fenn et al. |
| 6,726,651 B1 | 4/2004 | Robinson et al. |
| 6,728,334 B1 | 4/2004 | Zhao |
| 6,730,042 B2 | 5/2004 | Fulton et al. |
| 6,730,045 B2 | 5/2004 | Finer |
| 6,731,966 B1 | 5/2004 | Spigelman et al. |
| 6,733,969 B2 | 5/2004 | Mack |
| 6,738,663 B2 | 5/2004 | Schroeppel et al. |
| 6,746,844 B2 | 6/2004 | Oliner et al. |
| 6,750,015 B2 | 6/2004 | Horwitz et al. |
| 6,752,154 B2 | 6/2004 | Fogarty et al. |
| 6,752,767 B2 | 6/2004 | Turovskiy et al. |
| 6,752,768 B2 | 6/2004 | Burdorff et al. |
| 6,752,769 B2 | 6/2004 | Alberico |
| 6,753,138 B1 | 6/2004 | Schneider et al. |
| 6,758,848 B2 | 7/2004 | Burbank et al. |
| 6,764,449 B2 | 7/2004 | Lee et al. |
| 6,764,495 B2 | 7/2004 | Lee et al. |
| 6,766,186 B1 | 7/2004 | Hoyns et al. |
| 6,767,704 B2 | 7/2004 | Waldman et al. |
| 6,768,925 B2 | 7/2004 | Fenn et al. |
| 6,770,066 B1 | 8/2004 | Weaver et al. |
| 6,770,070 B1 | 8/2004 | Balbierz |
| 6,770,435 B1 | 8/2004 | Billing-Medel et al. |
| 6,770,770 B1 | 8/2004 | Baumann et al. |
| 6,773,903 B2 | 8/2004 | Bova |
| 6,776,757 B2 | 8/2004 | Larson et al. |
| 6,780,984 B2 | 8/2004 | Wang et al. |
| 6,785,410 B2 | 8/2004 | Vining et al. |
| 6,786,870 B2 | 9/2004 | Miyaki et al. |
| 6,788,977 B2 | 9/2004 | Fenn et al. |
| 6,790,185 B1 | 9/2004 | Fisher et al. |
| 6,797,477 B2 | 9/2004 | Guida et al. |
| 6,805,669 B2 | 10/2004 | Swanbom |
| 6,805,869 B2 | 10/2004 | Guo |
| 6,806,712 B2 | 10/2004 | Akgun |
| 6,807,444 B2 | 10/2004 | Tu et al. |
| 6,808,878 B1 | 10/2004 | Gray et al. |
| 6,818,184 B2 | 11/2004 | Fulwyler et al. |
| 6,818,750 B2 | 11/2004 | Reed |
| 6,819,785 B1 | 11/2004 | Vining et al. |
| 6,821,725 B1 | 11/2004 | Carrasco et al. |
| 6,824,780 B1 | 11/2004 | Devaux et al. |
| 6,824,974 B2 | 11/2004 | Pisharody et al. |
| 6,824,995 B1 | 11/2004 | Wu |
| 6,827,692 B2 | 12/2004 | Castellacci |
| 6,831,059 B2 | 12/2004 | Donovan |
| 6,832,111 B2 | 12/2004 | Tu et al. |
| 6,833,373 B1 | 12/2004 | McKeam et al. |
| 6,833,438 B1 | 12/2004 | Afar et al. |
| 6,835,183 B2 | 12/2004 | Lennox et al. |

(56) References Cited

U.S. PATENT DOCUMENTS

| | | |
|---|---|---|
| 6,835,572 B1 | 12/2004 | Mountford et al. |
| 6,838,243 B2 | 1/2005 | Lai et al. |
| 6,840,952 B2 | 1/2005 | Saker et al. |
| 6,841,350 B2 | 1/2005 | Ogden et al. |
| 6,843,980 B2 | 1/2005 | Green |
| 6,844,153 B2 | 1/2005 | Waldman et al. |
| 6,846,320 B2 | 1/2005 | Ashby et al. |
| 6,846,650 B2 | 1/2005 | Recipon et al. |
| 6,846,911 B2 | 1/2005 | Kelly |
| 6,847,841 B1 | 1/2005 | El Hatw |
| 6,849,080 B2 | 2/2005 | Lee et al. |
| 6,850,588 B2 | 2/2005 | Arenson et al. |
| 6,852,528 B2 | 2/2005 | Yu et al. |
| 6,855,517 B2 | 2/2005 | Salceda et al. |
| 6,855,554 B2 | 2/2005 | Fritsche et al. |
| 6,858,412 B2 | 2/2005 | Willis et al. |
| 6,858,598 B1 | 2/2005 | McKeam et al. |
| 6,858,711 B2 | 2/2005 | McGall et al. |
| 6,859,049 B2 | 2/2005 | Khatchatrian et al. |
| 6,860,855 B2 | 3/2005 | Shelby et al. |
| 6,860,860 B2 | 3/2005 | Viola |
| 6,863,676 B2 | 3/2005 | Lee et al. |
| 6,864,224 B1 | 3/2005 | Sedivy et al. |
| 6,866,630 B2 | 3/2005 | Larson et al. |
| 6,866,993 B1 | 3/2005 | Williamson |
| 6,866,994 B2 | 3/2005 | Morton |
| 6,867,016 B1 | 3/2005 | Billing-Medel et al. |
| 6,867,753 B2 | 3/2005 | Chinthammit et al. |
| 6,871,086 B2 | 3/2005 | Nevo et al. |
| 6,872,184 B2 | 3/2005 | Brannon |
| 6,872,185 B2 | 3/2005 | Fisher |
| 6,872,389 B1 | 3/2005 | Fads |
| 6,875,182 B2 | 4/2005 | Wardie et al. |
| 6,875,184 B2 | 4/2005 | Morton et al. |
| 6,883,194 B2 | 4/2005 | Corbeil et al. |
| 6,883,958 B2 | 4/2005 | Mayer |
| 6,884,578 B2 | 4/2005 | Warington et al. |
| 6,884,605 B2 | 4/2005 | Hermonat et al. |
| 6,887,210 B2 | 5/2005 | Quay |
| 6,888,919 B2 | 5/2005 | Graf |
| 6,890,308 B2 | 5/2005 | Islam |
| 6,890,309 B2 | 5/2005 | Fisher |
| 6,890,311 B2 | 5/2005 | Love et al. |
| 6,890,749 B2 | 5/2005 | Billing-Medel et al. |
| 6,893,818 B1 | 5/2005 | Afar et al. |
| 6,893,868 B2 | 5/2005 | Packard et al. |
| 6,894,026 B1 | 5/2005 | Quay |
| 6,899,696 B2 | 5/2005 | Morton et al. |
| 6,900,015 B2 | 5/2005 | Avihingsanon et al. |
| 6,900,049 B2 | 5/2005 | Yu et al. |
| 6,901,278 B1 | 5/2005 | Notelovitz |
| 6,904,305 B2 | 6/2005 | Tsekos |
| 6,904,309 B2 | 6/2005 | Derendorf et al. |
| 6,905,475 B2 | 6/2005 | Hauschild et al. |
| 6,908,440 B2 | 6/2005 | Fisher |
| 6,913,882 B2 | 7/2005 | Glynne et al. |
| 6,914,130 B2 | 7/2005 | Gao et al. |
| 6,916,800 B2 | 7/2005 | McKearn et al. |
| 6,916,918 B2 | 7/2005 | Yu et al. |
| 6,918,881 B2 | 7/2005 | Miller et al. |
| 6,919,176 B2 | 7/2005 | Yang et al. |
| 6,920,347 B2 | 7/2005 | Simon et al. |
| RE38,776 E | 8/2005 | Bauer |
| 6,923,809 B2 | 8/2005 | Eggers et al. |
| 6,924,094 B1 | 8/2005 | Gingeras et al. |
| 6,925,389 B2 | 8/2005 | Hitt et al. |
| 6,926,893 B1 | 8/2005 | Hansen |
| 6,927,032 B2 | 8/2005 | Lockhart et al. |
| 6,933,105 B2 | 8/2005 | Jin |
| 6,936,014 B2 | 8/2005 | Vetter et al. |
| 6,936,416 B2 | 8/2005 | Zhu et al. |
| 6,936,687 B1 | 8/2005 | Komoriya et al. |
| 6,942,985 B2 | 9/2005 | Waldman |
| 6,943,236 B2 | 9/2005 | Xu et al. |
| 6,944,505 B2 | 9/2005 | Zhang et al. |
| 6,945,942 B2 | 9/2005 | Van Bladel et al. |
| 6,947,584 B1 | 9/2005 | Avila et al. |
| 6,949,357 B2 | 9/2005 | Billing-Medel et al. |
| 6,953,691 B2 | 10/2005 | Reed et al. |
| 6,954,667 B2 | 10/2005 | Treado et al. |
| 6,955,653 B2 | 10/2005 | Eggers |
| 6,965,793 B2 | 11/2005 | Treado et al. |
| 6,994,712 B1 | 2/2006 | Fisher et al. |
| D518,175 S | 3/2006 | Hardin, Jr. et al. |
| 7,014,610 B2 | 3/2006 | Koulik |
| 7,025,765 B2 | 4/2006 | Balbierz et al. |
| 7,067,111 B1 | 6/2006 | Yang et al. |
| 7,067,274 B2 | 6/2006 | Fairbrother et al. |
| 7,070,816 B2 | 7/2006 | Newmark et al. |
| 7,072,704 B2 | 7/2006 | Bucholz |
| 7,074,600 B2 | 7/2006 | Dean et al. |
| 7,077,842 B1 | 7/2006 | Cosman |
| 7,079,132 B2 | 7/2006 | Sauer et al. |
| 7,081,340 B2 | 7/2006 | Baker et al. |
| 7,083,547 B2 | 8/2006 | LaStayo et al. |
| 7,083,985 B2 | 8/2006 | Hefti et al. |
| 7,087,393 B2 | 8/2006 | Billing-Medel et al. |
| 7,089,121 B1 | 8/2006 | Wang |
| 7,090,845 B2 | 8/2006 | Fong et al. |
| 7,090,862 B2 | 8/2006 | Barrett-Reis et al. |
| 7,091,047 B2 | 8/2006 | Serrero |
| 7,094,233 B2 | 8/2006 | Desinger |
| 7,101,663 B2 | 9/2006 | Godfrey et al. |
| 7,101,862 B2 | 9/2006 | Cochrum et al. |
| 7,108,969 B1 | 9/2006 | Warrangton et al. |
| 7,115,368 B2 | 10/2006 | Powers et al. |
| 7,118,876 B2 | 10/2006 | Tyner et al. |
| 7,118,910 B2 | 10/2006 | Unger et al. |
| 7,122,011 B2 | 10/2006 | Clifford et al. |
| 7,122,653 B2 | 10/2006 | Cohen et al. |
| 7,125,836 B2 | 10/2006 | Woodward |
| 7,125,969 B1 | 10/2006 | Benz et al. |
| 7,128,877 B2 | 10/2006 | Quay et al. |
| 7,128,893 B2 | 10/2006 | Leamon et al. |
| 7,129,048 B2 | 10/2006 | Bruchez et al. |
| 7,131,951 B2 * | 11/2006 | Angel .................... 600/567 |
| 7,135,333 B1 | 11/2006 | Waldman et al. |
| 7,139,601 B2 | 11/2006 | Bucholz et al. |
| 7,141,019 B2 | 11/2006 | Pearlman |
| 7,144,950 B2 | 12/2006 | Bazan et al. |
| 7,153,700 B1 | 12/2006 | Pardee et al. |
| 7,156,814 B1 | 1/2007 | Williamson, IV et al. |
| 7,156,815 B2 | 1/2007 | Leigh et al. |
| 7,160,292 B2 | 1/2007 | Moorman et al. |
| 7,161,057 B2 | 1/2007 | Kneteman et al. |
| 7,169,114 B2 | 1/2007 | Krause |
| 7,172,558 B2 | 2/2007 | Olson, Jr. |
| 7,172,739 B2 | 2/2007 | Maughan |
| 7,175,839 B1 | 2/2007 | Hiserodt |
| 7,183,251 B1 | 2/2007 | Russo et al. |
| D538,933 S | 3/2007 | Andrade |
| 7,186,522 B2 | 3/2007 | Lapen et al. |
| 7,189,206 B2 | 3/2007 | Quick et al. |
| 7,189,207 B2 | 3/2007 | Viola |
| 7,190,378 B2 | 3/2007 | Sauer et al. |
| 7,192,570 B2 | 3/2007 | Maecke et al. |
| 7,195,774 B2 | 3/2007 | Carvalho et al. |
| 7,195,868 B2 | 3/2007 | Iartchouk et al. |
| 7,195,911 B2 | 3/2007 | Cech et al. |
| 7,196,182 B2 | 3/2007 | Reed et al. |
| 7,198,896 B2 | 4/2007 | Rush et al. |
| 7,199,234 B2 | 4/2007 | Morin et al. |
| 7,204,988 B2 | 4/2007 | Cheung |
| 7,207,985 B2 | 4/2007 | Duong et al. |
| 7,208,146 B2 | 4/2007 | Denney, Jr. |
| 7,208,267 B2 | 4/2007 | Salceda et al. |
| 7,211,398 B2 | 5/2007 | Astle et al. |
| 7,214,489 B2 | 5/2007 | Bazan et al. |
| 7,217,276 B2 | 5/2007 | Henderson et al. |
| 7,217,394 B2 | 5/2007 | Studer |
| 7,218,959 B2 | 5/2007 | Alfano et al. |
| 7,220,258 B2 | 5/2007 | Myhr |
| 7,220,891 B2 | 5/2007 | Barsky et al. |
| 7,223,238 B2 | 5/2007 | Swanbom |

(56) References Cited

U.S. PATENT DOCUMENTS

| | | | |
|---|---|---|---|
| 7,223,380 B2 | 5/2007 | Yang et al. | |
| 7,223,540 B2 | 5/2007 | Pourmand et al. | |
| 7,223,542 B2 | 5/2007 | Raitano et al. | |
| 7,226,731 B1 | 6/2007 | Chuaqui et al. | |
| 7,227,009 B2 | 6/2007 | Craik et al. | |
| 7,229,413 B2 | 6/2007 | Violante et al. | |
| 7,229,417 B2 | 6/2007 | Foerster et al. | |
| 7,229,439 B2 | 6/2007 | Burbank et al. | |
| 7,229,604 B2 | 6/2007 | Yang et al. | |
| 7,229,774 B2 | 6/2007 | Chinnaiyan et al. | |
| 7,231,015 B2 | 6/2007 | Kumakhov | |
| 7,235,047 B2 | 6/2007 | MacAulay et al. | |
| 7,236,816 B2 | 6/2007 | Kumar et al. | |
| 7,241,736 B2 | 7/2007 | Hunter et al. | |
| 7,244,619 B2 | 7/2007 | Contreras et al. | |
| 7,245,748 B2 | 7/2007 | Degani et al. | |
| 7,245,958 B1 | 7/2007 | Navab et al. | |
| 7,247,426 B2 | 7/2007 | Yakhini et al. | |
| 7,250,180 B2 | 7/2007 | Arellano | |
| 7,250,264 B2 | 7/2007 | Fong et al. | |
| 7,250,551 B2 | 7/2007 | Tsai et al. | |
| 7,251,352 B2 | 7/2007 | Sauer et al. | |
| 7,251,568 B2 | 7/2007 | Pittman et al. | |
| 7,252,935 B2 | 8/2007 | Sidransky | |
| 7,252,946 B2 | 8/2007 | Szasz | |
| 7,252,948 B2 | 8/2007 | Gingeras et al. | |
| 7,258,973 B2 | 8/2007 | Astle et al. | |
| 7,261,712 B2 | 8/2007 | Burbank et al. | |
| 7,261,875 B2 | 8/2007 | Li et al. | |
| 7,262,288 B1 | 8/2007 | Cech et al. | |
| 7,264,947 B2 | 9/2007 | Gozes et al. | |
| 7,270,956 B2 | 9/2007 | Bazan et al. | |
| 7,271,187 B2 | 9/2007 | Neuberger et al. | |
| 7,274,810 B2 | 9/2007 | Reeves et al. | |
| 7,314,481 B2 | 1/2008 | Karpiel | |
| 7,608,056 B2 | 10/2009 | Kennedy, II | |
| 8,109,953 B1 | 2/2012 | King, III et al. | |
| D657,461 S | 4/2012 | Schembre et al. | |
| 8,162,958 B2 | 4/2012 | Takahashi et al. | |
| 8,187,203 B2 | 5/2012 | McClellan | |
| 8,262,680 B2 | 9/2012 | Swain et al. | |
| 8,328,772 B2 | 12/2012 | Kinast et al. | |
| 8,357,193 B2 | 1/2013 | Phan et al. | |
| 8,361,041 B2 | 1/2013 | Fang et al. | |
| 8,454,632 B2 | 6/2013 | Binmoeller et al. | |
| 8,486,010 B2 | 7/2013 | Nomura | |
| D690,009 S | 9/2013 | Schembre et al. | |
| 8,968,210 B2 | 3/2015 | Mugan et al. | |
| 9,186,128 B2 | 11/2015 | Mugan et al. | |
| 2001/0007925 A1 | 7/2001 | Ritchart et al. | |
| 2001/0023322 A1 | 9/2001 | Espositio et al. | |
| 2001/0047183 A1 | 11/2001 | Privitera et al. | |
| 2001/0056218 A1 | 12/2001 | Hogendijk et al. | |
| 2002/0035324 A1 | 3/2002 | Sirimanne et al. | |
| 2002/0082519 A1 | 6/2002 | Miller et al. | |
| 2002/0156395 A1 | 10/2002 | Stephens et al. | |
| 2002/0169418 A1 | 11/2002 | Menzi et al. | |
| 2003/0078502 A1 | 4/2003 | Miyaki et al. | |
| 2003/0093007 A1 | 5/2003 | Wood | |
| 2003/0105488 A1 | 6/2003 | Chu | |
| 2003/0139752 A1* | 7/2003 | Pasricha et al. | 606/139 |
| 2003/0163142 A1 | 8/2003 | Paltieli et al. | |
| 2003/0181823 A1 | 9/2003 | Gatto | |
| 2003/0195436 A1 | 10/2003 | Van Bladel et al. | |
| 2003/0204137 A1 | 10/2003 | Chesbrough et al. | |
| 2003/0208134 A1 | 11/2003 | Secrest et al. | |
| 2003/0208219 A1 | 11/2003 | Aznolan et al. | |
| 2003/0212394 A1 | 11/2003 | Pearson et al. | |
| 2003/0233101 A1 | 12/2003 | Lubock et al. | |
| 2004/0073219 A1 | 4/2004 | Skiba et al. | |
| 2004/0077948 A1 | 4/2004 | Violante et al. | |
| 2004/0153005 A1 | 8/2004 | Krueger | |
| 2004/0167429 A1 | 8/2004 | Roshdieh et al. | |
| 2004/0236212 A1 | 11/2004 | Jones et al. | |
| 2004/0249395 A1 | 12/2004 | Mikkaichi et al. | |
| 2004/0260199 A1 | 12/2004 | Hardia et al. | |
| 2004/0260274 A1 | 12/2004 | Hardin et al. | |
| 2005/0021003 A1 | 1/2005 | Caso et al. | |
| 2005/0022493 A1 | 2/2005 | Olinger et al. | |
| 2005/0061697 A1 | 3/2005 | Moberg | |
| 2005/0113715 A1 | 5/2005 | Schwindt et al. | |
| 2005/0143753 A1 | 6/2005 | Whitmore et al. | |
| 2005/0159676 A1 | 7/2005 | Taylor et al. | |
| 2005/0192535 A1 | 9/2005 | Takagi et al. | |
| 2005/0197623 A1* | 9/2005 | Leeflang et al. | 604/95.04 |
| 2005/0228311 A1 | 10/2005 | Beckman et al. | |
| 2005/0228312 A1 | 10/2005 | Surti | |
| 2005/0228413 A1 | 10/2005 | Binmoeller et al. | |
| 2005/0251111 A1 | 11/2005 | Saito et al. | |
| 2005/0256426 A1 | 11/2005 | Brugge | |
| 2005/0272975 A1 | 12/2005 | McWeeney et al. | |
| 2006/0052750 A1 | 3/2006 | Lenker et al. | |
| 2006/0100654 A1 | 5/2006 | Fukuda et al. | |
| 2006/0116605 A1 | 6/2006 | Nakao | |
| 2006/0142789 A1 | 6/2006 | Lehman et al. | |
| 2006/0155210 A1 | 7/2006 | Beckman et al. | |
| 2006/0167416 A1 | 7/2006 | Mathis et al. | |
| 2006/0189891 A1 | 8/2006 | Waxman et al. | |
| 2006/0235298 A1 | 10/2006 | Kotmel et al. | |
| 2006/0247530 A1 | 11/2006 | Hardin et al. | |
| 2006/0258955 A1 | 11/2006 | Hoffman et al. | |
| 2006/0264919 A1 | 11/2006 | Schaaf | |
| 2007/0023304 A1 | 2/2007 | Joyce et al. | |
| 2007/0032741 A1 | 2/2007 | Hibner et al. | |
| 2007/0038089 A1 | 2/2007 | Hatano et al. | |
| 2007/0055173 A1 | 3/2007 | DeLonzor et al. | |
| 2007/0056360 A1 | 3/2007 | Grant et al. | |
| 2007/0060837 A1 | 3/2007 | Cho et al. | |
| 2007/0118049 A1 | 5/2007 | Viola | |
| 2007/0123799 A1 | 5/2007 | Meireles | |
| 2007/0123800 A1 | 5/2007 | Nishtala et al. | |
| 2007/0149893 A1 | 6/2007 | Heske et al. | |
| 2007/0177009 A1 | 8/2007 | Bayer et al. | |
| 2007/0179403 A1 | 8/2007 | Heske et al. | |
| 2007/0185411 A1 | 8/2007 | Hibner | |
| 2007/0213633 A1 | 9/2007 | McClellan | |
| 2007/0213634 A1 | 9/2007 | Teague | |
| 2007/0299306 A1 | 12/2007 | Parasher et al. | |
| 2008/0058637 A1 | 3/2008 | Fischell et al. | |
| 2008/0097344 A1 | 4/2008 | McKinnon et al. | |
| 2008/0146962 A1 | 6/2008 | Ritchie et al. | |
| 2008/0200912 A1 | 8/2008 | Long | |
| 2008/0294111 A1 | 11/2008 | Tal et al. | |
| 2008/0300462 A1 | 12/2008 | Intoccia et al. | |
| 2008/0319341 A1 | 12/2008 | Taylor et al. | |
| 2009/0054773 A1* | 2/2009 | Shizuka | 600/439 |
| 2009/0069679 A1 | 3/2009 | Hibi | |
| 2009/0099414 A1 | 4/2009 | Goto et al. | |
| 2009/0177114 A1 | 7/2009 | Chin et al. | |
| 2009/0182200 A1 | 7/2009 | Golden et al. | |
| 2009/0264794 A1* | 10/2009 | Kodama | 600/567 |
| 2009/0312645 A1 | 12/2009 | Weitzner et al. | |
| 2010/0010453 A1* | 1/2010 | Riemelmoser | A61M 5/3243 604/198 |
| 2010/0081965 A1 | 4/2010 | Mugan et al. | |
| 2010/0121218 A1 | 5/2010 | Mugan et al. | |
| 2010/0274085 A1 | 10/2010 | Mugan et al. | |
| 2011/0054381 A1 | 3/2011 | Van Dam et al. | |
| 2011/0071350 A1 | 3/2011 | Van Dam et al. | |
| 2011/0137394 A1 | 6/2011 | Lunsford et al. | |
| 2011/0152886 A1 | 6/2011 | Sato et al. | |
| 2012/0029278 A1 | 2/2012 | Sato et al. | |
| 2012/0116248 A1 | 5/2012 | McWeeney et al. | |
| 2012/0136426 A1 | 5/2012 | Phan et al. | |
| 2012/0157880 A1 | 6/2012 | Haselby et al. | |
| 2012/0245486 A1 | 9/2012 | Melchiorri et al. | |
| 2012/0253228 A1 | 10/2012 | Schembre et al. | |
| 2012/0296257 A1 | 11/2012 | Van Dam et al. | |
| 2013/0041286 A1 | 2/2013 | Theobald et al. | |
| 2013/0110141 A1 | 5/2013 | Chmura | |
| 2013/0131547 A1 | 5/2013 | Hardert et al. | |
| 2013/0131548 A1 | 5/2013 | McGhie et al. | |
| 2013/0253546 A1 | 9/2013 | Sander et al. | |
| 2013/0253550 A1 | 9/2013 | Beisel et al. | |

(56) References Cited

U.S. PATENT DOCUMENTS

| | | | |
|---|---|---|---|
| 2013/0310833 A1 | 11/2013 | Brown et al. | |
| 2013/0325038 A1 | 12/2013 | Sato | |
| 2014/0005478 A1 | 1/2014 | Kennedy, II et al. | |
| 2014/0088684 A1 | 3/2014 | Paskar | |

FOREIGN PATENT DOCUMENTS

| | | | |
|---|---|---|---|
| EP | 0739640 A1 | 10/1996 | |
| EP | 1870051 A1 | 12/2007 | |
| EP | 1870051 A1 | 12/2007 | |
| EP | 2030574 A2 | 3/2009 | |
| EP | 2030574 A2 | 4/2009 | |
| JP | 06189965 H | 7/1994 | |
| JP | 7116169 H | 5/1995 | |
| JP | 8-38482 A | 3/1996 | |
| JP | 9-135836 A | 5/1997 | |
| JP | 2005058431 A | 3/2005 | |
| WO | 9204062 A1 | 3/1992 | |
| WO | 2000033909 | 6/2000 | |
| WO | 2000033909 A1 | 6/2000 | |
| WO | 2005060835 A2 | 7/2005 | |
| WO | 2005096953 A2 | 10/2005 | |
| WO | 2005096963 A2 | 10/2005 | |
| WO | 2012112202 A1 | 8/2012 | |
| WO | 2013074653 A1 | 5/2013 | |

OTHER PUBLICATIONS

Notice of Allowance for JP 2014-542405 dated Oct. 6, 2016 from the Japanese Patent Office.

Creganna Needle Brochure, published Jan. 16, 2008.

Iglesias-Garcia, 2011, Feasibility and Yield of a New EUS Histology Needle: Results From a Multicenter, Pooled, Cohort Study, Gastrointestinal Endoscopy 73(6); 1189-1196.

Iwashita, 2013, High Single-Pass Diagnostic Yield of a new 25-Gauge Core Biopsy Needle for EUS-Guided FNa biopsy in Solid Pancreatic Lesions, Gastrointestinal Endoscopy 77(6); 909-915.

Kahaleh, 2013, Endoscopic Ultrasonography guided biliary drainage: Summary of consortium meeting, May 7, 2011 Chicago, World Journal of Gastroenterology, 19(9); 1372-1379.

Khashab, 2013, EUS-Guided biliary Drainage by Using a standardized approach for Malignant Biliary Obstruction: Rendezvous Versus Direct Transluminal techniques, Gastrointestinal Endoscopy; 1-8.

Park, 2011, EUS-guided Biliary Drainage with Transluminal stenting after Failed ERCP: predictors of Adverse Events and Long-Term Results, Gastrointestinal Endoscopy 74(6); 1276-1284.

Park, 2013, Prospective Evaluation of a Treatment Algorithm With Enhanced Guidewire Manipulation Protocol for EUS-Guided Biliary Drainage After failed ERCP, Gastrointestinal Endoscopy 78(1); 92-101.

Pelaez-Luna, 2008, Interventional EUS Guided Cholangiography. First Description in Mexico of a Novel, Secure and Feasible Technique. A Case Report, Caso Clinico.

Patent Examination Report No. 1 from the Australian Patent Office for Patent Application No. 2015207938 dated Jul. 9, 2016.

Canadian Office Action for App. No. 2,744,612 from the Canadian Intellectual Property Office dated Oct. 27, 2016.

Notice of Reasons for Rejection for JP App. No. 2014-236354 dated Dec. 9, 2015.

Examination report from Canadian Intellectual Property Office for App. No. 2,899,073 dated May 6, 2016.

Notice of Reasons for Rejection, dated Jun. 17, 2016, for Japanese Patent Application No. 2014-542405, from Japanese Patent Office.

Examiner's Report for Canadian Application No. 2,995,281 dated Oct. 19, 2018.

Examination Report for Canadian App. No. 2,856,060 dated Aug. 15, 2019 from the Canadian Intellectual Property Office.

\* cited by examiner

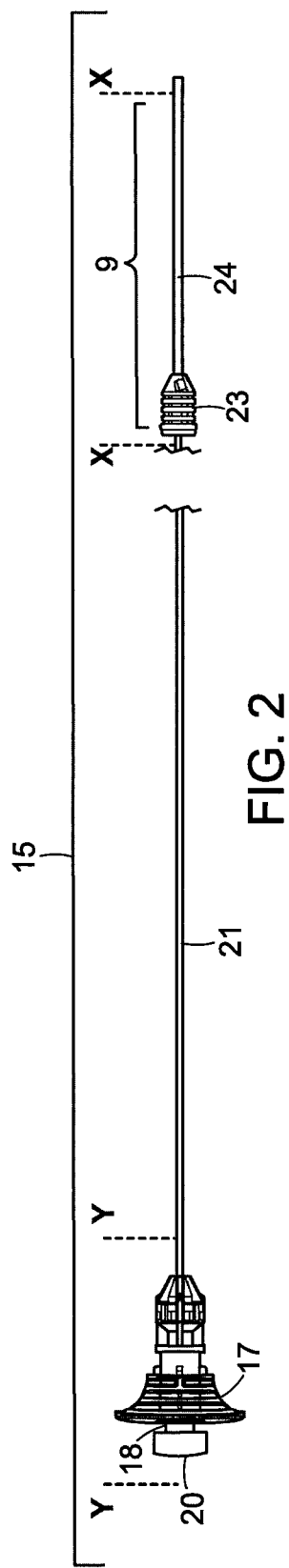
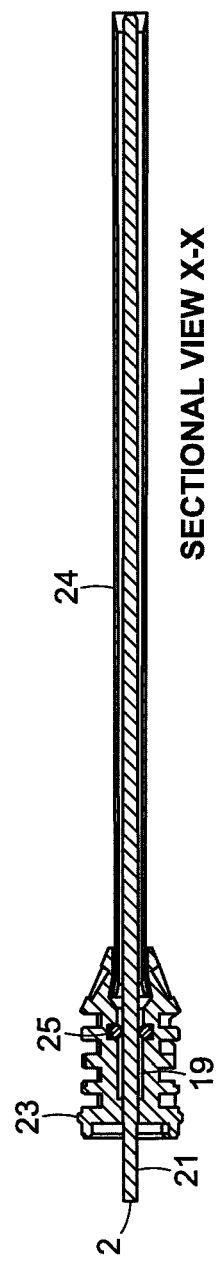
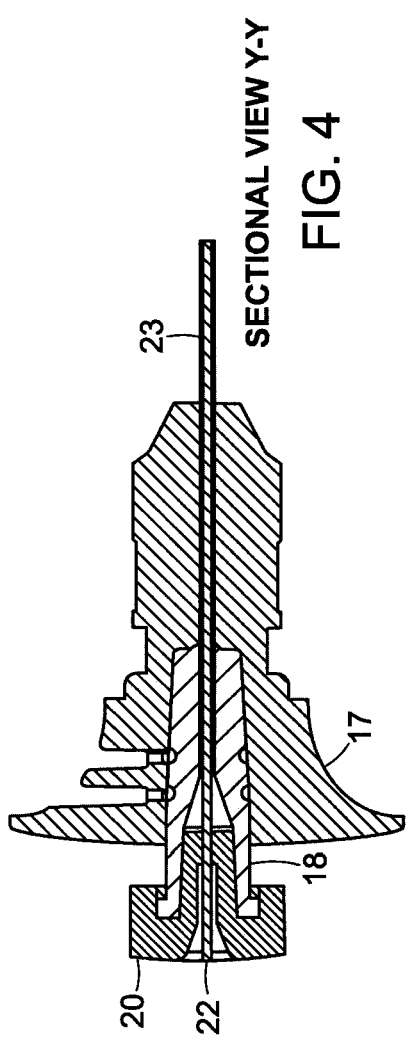
FIG. 2
SECTIONAL VIEW X-X
FIG. 3
SECTIONAL VIEW Y-Y
FIG. 4

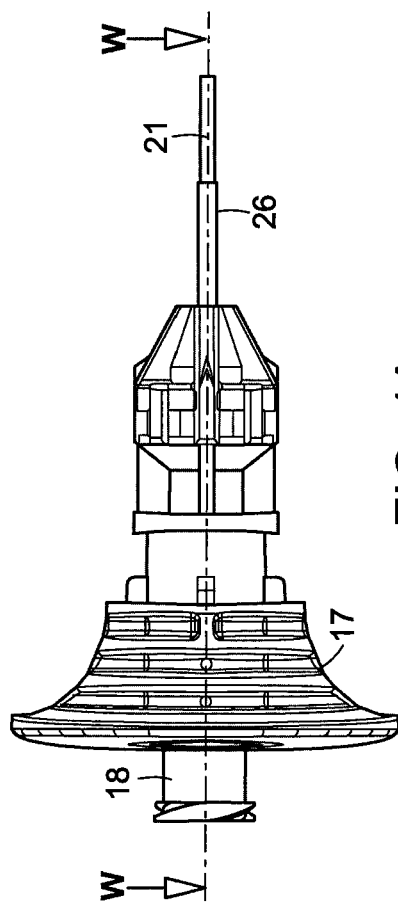
FIG. 4A
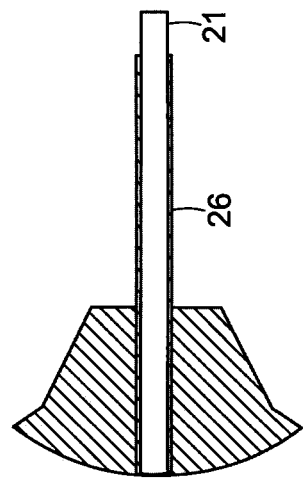
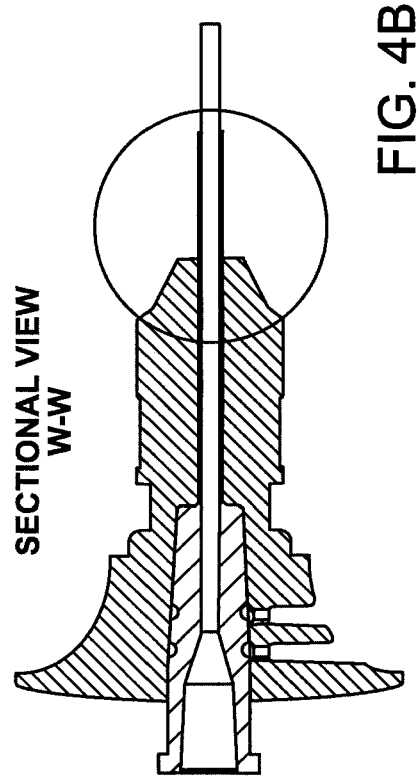
FIG. 4B

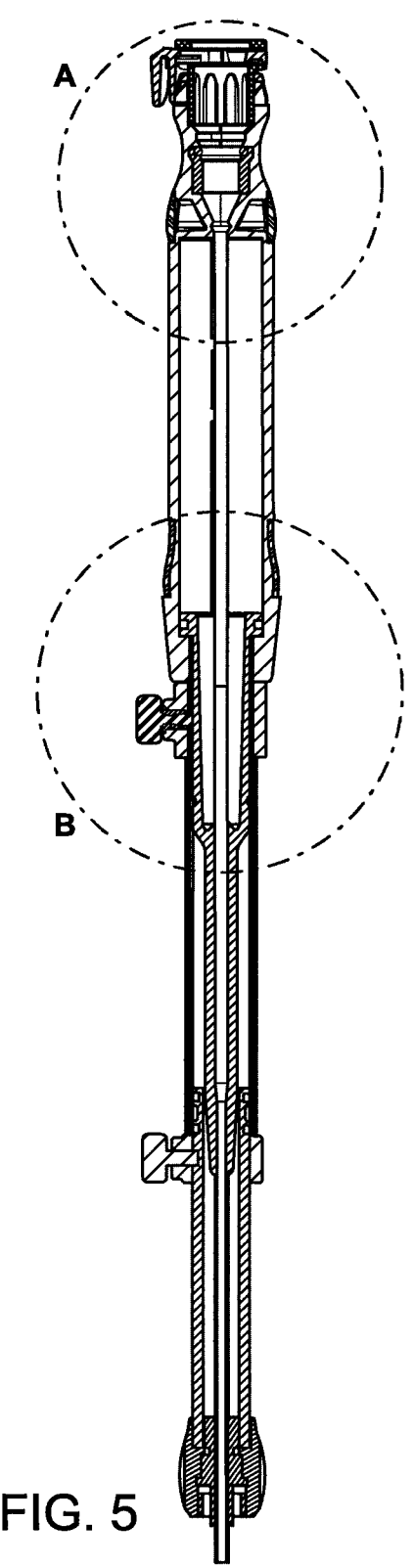
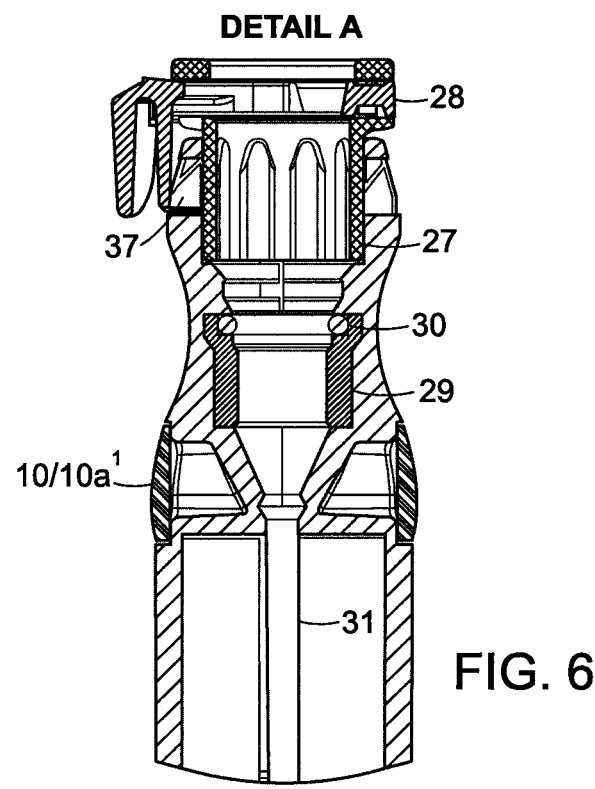
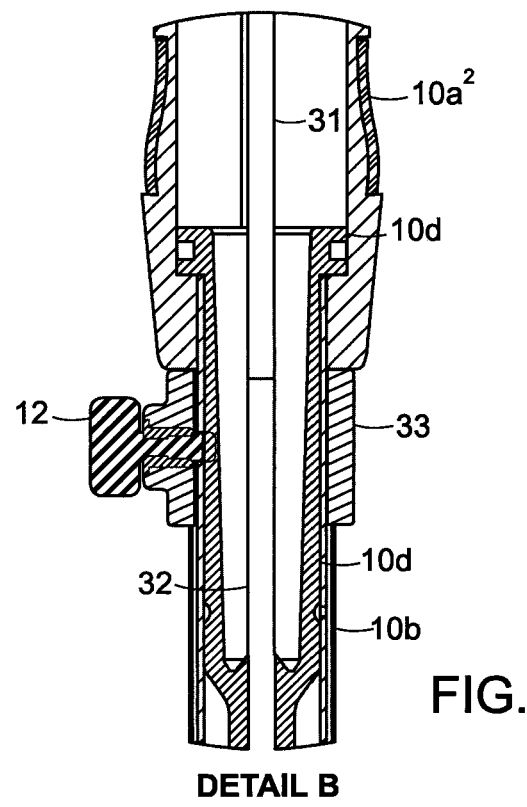
FIG. 5
FIG. 6
FIG. 7

DETAIL C

DETAIL D

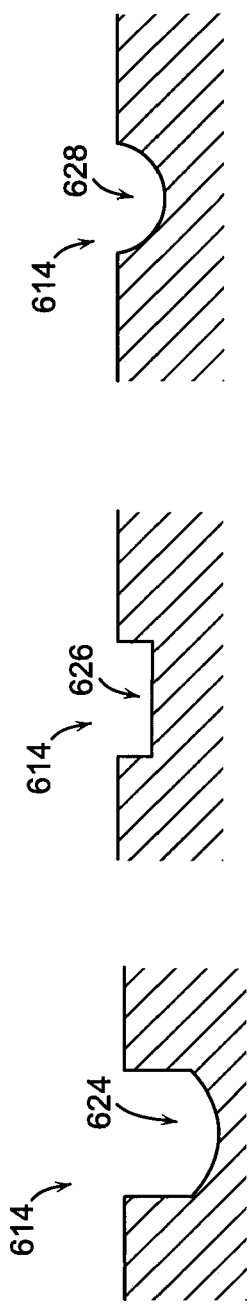
FIG. 10L
FIG. 10M
FIG. 10N
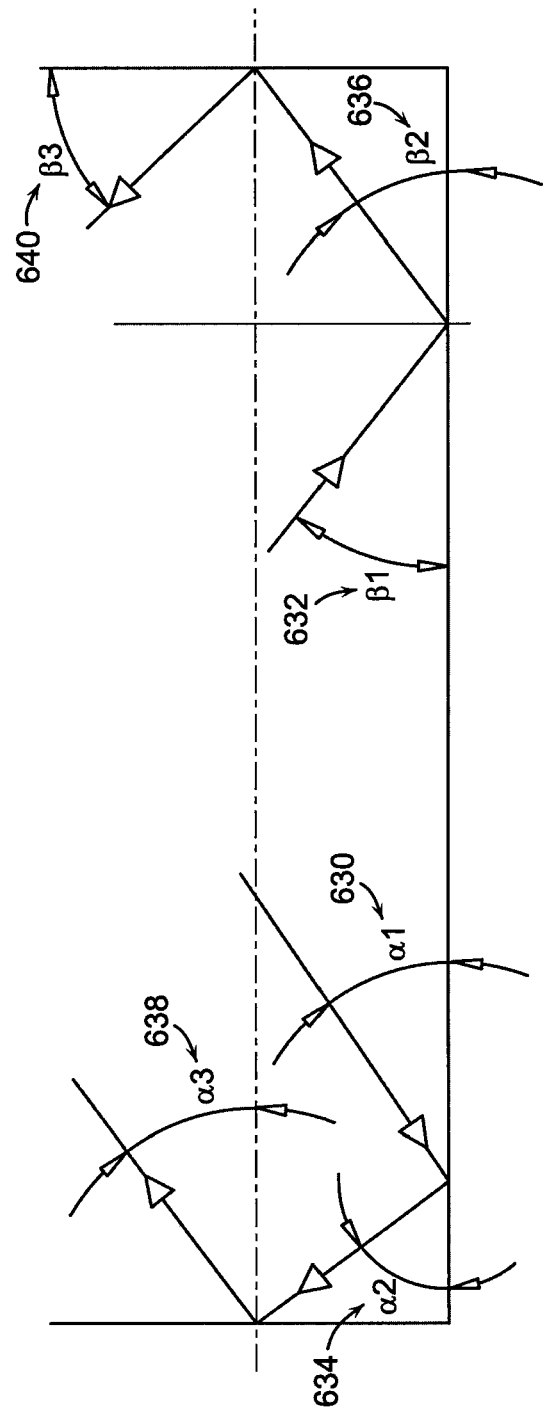
FIG. 10O

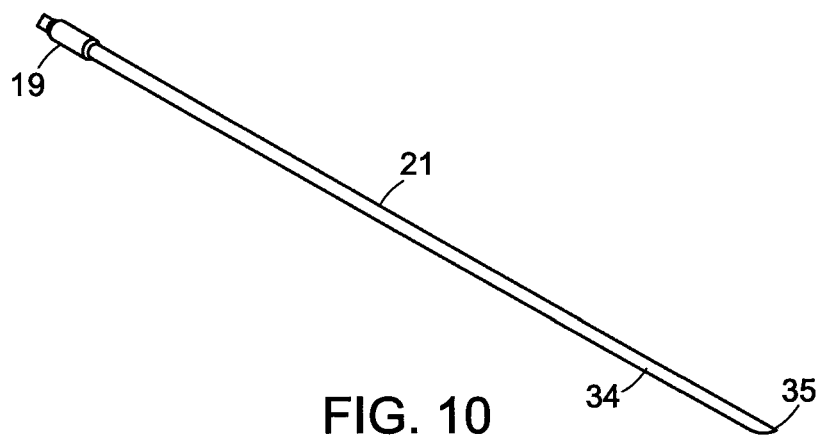
FIG. 10
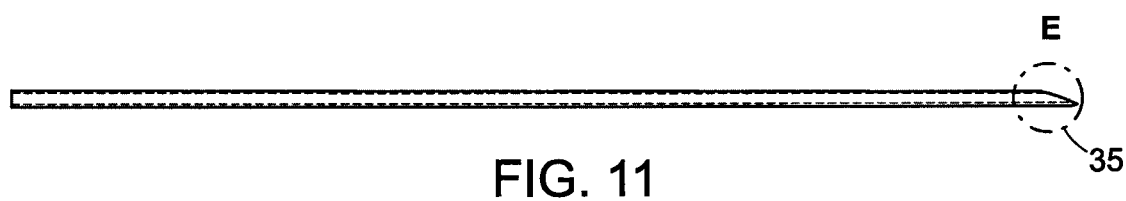
FIG. 11
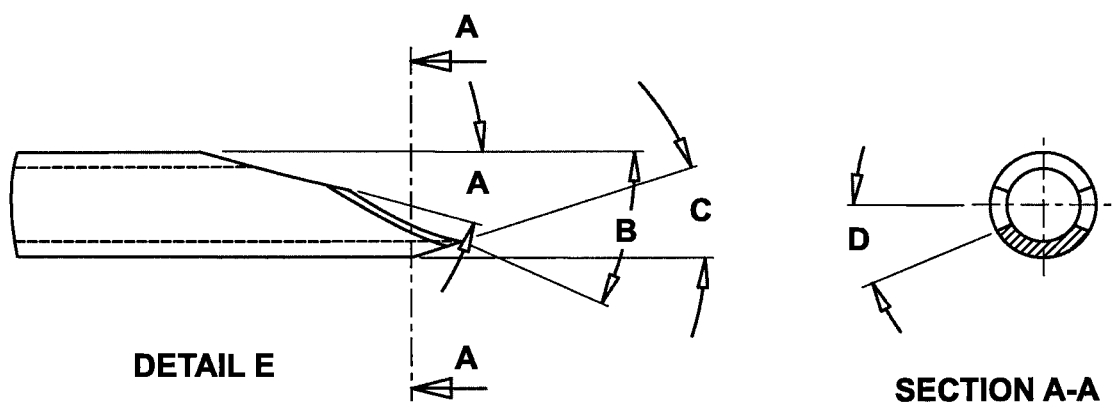
DETAIL E
FIG. 12
SECTION A-A
FIG. 13

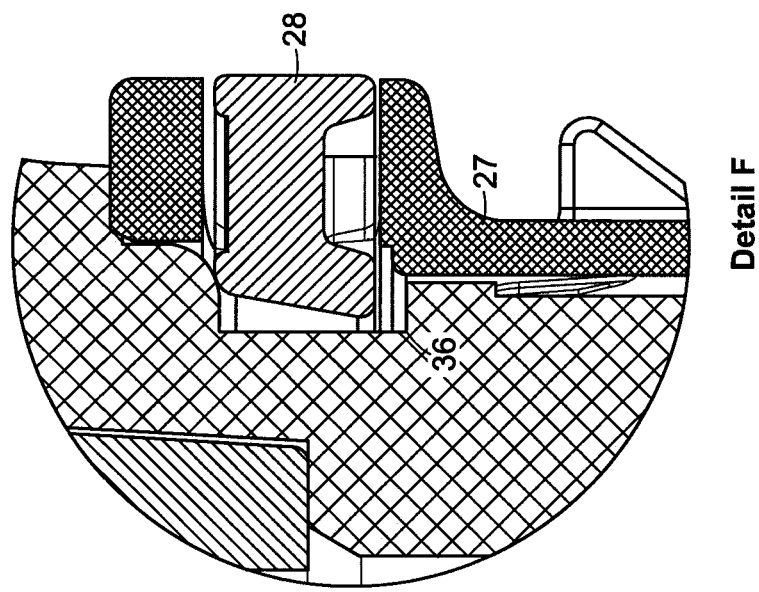
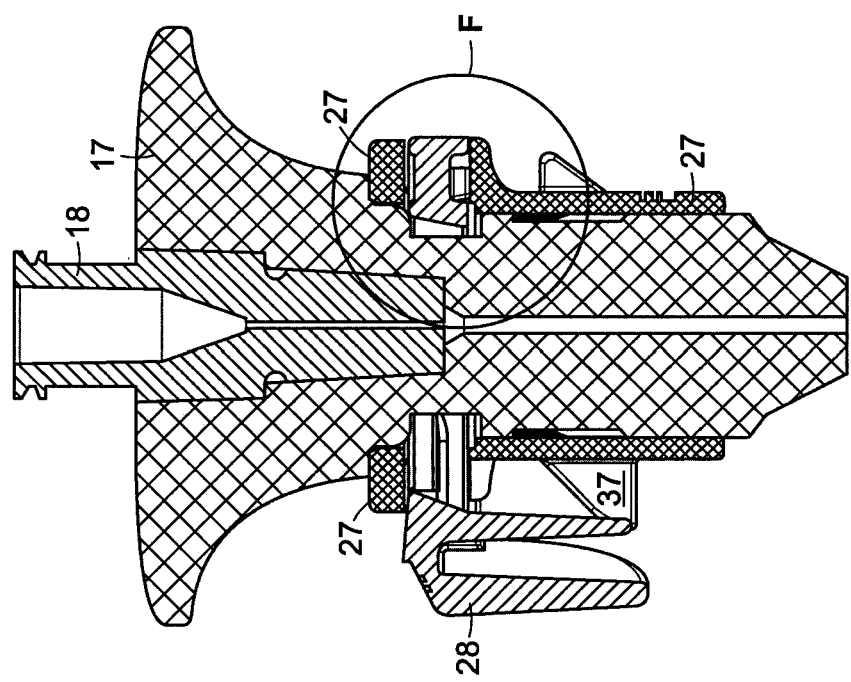
FIG. 19

DETAIL G

NEEDLE BIOPSY DEVICE WITH EXCHANGEABLE NEEDLE AND INTEGRATED NEEDLE PROTECTION

CROSS-REFERENCE TO RELATED APPLICATIONS

This patent application is a continuation of U.S. Ser. No. 13/297,766, filed Nov. 16, 2011, which is a continuation-in-part of U.S. Ser. No. 13/029,593 filed Feb. 17, 2011, which claims priority to U.S. Ser. No. 61/305,304, filed Feb. 17, 2010, and U.S. Ser. No. 61/305,396 filed Feb. 17, 2010. U.S. Ser. No. 13/297,766 is also; a continuation-in-part of U.S. Ser. No. 12/607,636, filed Oct. 28, 2009 (now U.S. Pat. No. 8,068,210), which claims priority to U.S. Ser. No. 61/117,966, filed Nov. 26, 2008, and U.S. Ser. No. 61/152,741, filed Feb. 16, 2009. U.S. Ser. No. 13/297,766 is also; a continuation-in-part of U.S. Ser. No. 12/243,367, filed Oct. 1, 2008 (now U.S. Pat. No. 9,186,128). The entire contents of each of the above-mentioned applications are incorporated by reference herein.

TECHNICAL FIELD

The present disclosure generally relates to the biopsy devices, and more particularly, needle biopsy devices for collecting tissue, fluid, and cell samples in conjunction with procedures such as endoscopic ultrasound or endoscopic bronchial ultrasound.

BACKGROUND INFORMATION

Endoscopic ultrasounds have been used for more than twenty five years within the field of medicine. These procedures allow clinicians to scan, locate and identify individual layers of the gastrointestinal (GI) tract and determine the location of individual mucosal and submucosal layers. As a result, appropriate therapeutic modes of treatment for malignancies and various abnormalities may be determined.

Endoscopic Ultrasound-Guided Fine-Needle Aspiration ("EUS—FNA") and Endobronchial Ultrasound-Guided Fine-Needle Aspiration ("EBUS—FNA") are currently standard modes of treatment in the field of GI Endoscopy and Bronchoscopy with high yields of sensitivity and specificity in the management of indications/diseases such as esophageal cancer, pancreatic cancer, liver mass, non-small cell lung cancer, pancreatic mass, endobronchial mass, and intra-abdominal lymph nodes.

A typical endoscopic ultrasound procedure consist of several steps. First, a clinician sedates a patient and inserts a probe via esophagogastroduodenoscopy into the patient's stomach and duodenum. Second, an endoscope is passed through the patient's mouth and advanced to the level of the duodenum. Third, from various positions between the esophagus and duodenum, organs or masses outside the gastrointestinal tract are imaged to determine abnormalities. If any abnormalities that are present, the organs and/or masses can be biopsied through the process of "fine needle aspiration" (FNA).

Endoscopic ultrasounds and endoscopic bronchial ultrasounds through fine needle aspiration are presently the standard modes of diagnosis and/or treatment in the field of gastrointestinal endoscopy and bronchoscopy. These procedures traditionally result in high yields of sensitivity and specificity in the management of indications of diseases such as esophageal cancer, pancreatic cancer, liver mass, non-small cell lung cancer, pancreatic mass, endobronchial mass, and intra-abdominal lymph nodes.

An endoscopic ultrasound through fine needle aspiration requires a device that is attached to the luer port or working channel of a typical echoendoscope. Prior art devices utilize a series of push and pull handles to control the axial movement of the catheter shaft of the device and the depth of needle penetration. These devices, however, suffer from several drawbacks.

One primary drawback of current FNA devices, concerns the lack of "Needle Safe Preventative" design features which protect the end user from inadvertent needle penetration and the transfer of blood-borne pathogens from patient subject to attending medical staff (Ref: The Needle-stick Safety and Prevention Act (HR 5178)—OSHA Regulation).

One of the primary issues still facing the medial device industry concerns the propensity for "Needle Stick". The Occupational Health and Safety Administration (OSHA) has warned that most needle destruction devices (NDDs) are "not compliant" with the Bloodborne Pathogens Standard, which are defined as " . . . controls (e.g., sharps disposal containers, self-sheathing needles, safer medical devices, such as sharps with engineered sharps injury protection and needleless systems) that isolate or remove the bloodborne pathogens hazard from the workplace." To comply with the OSHA standard, an employer must use engineering and work practice controls that will "eliminate or minimize employee exposure" (OSHA Sec. 1910.1030(d)(2)(i)). OSHA's compliance directive explains that under this requirement "the employer must use engineering and work practice controls that eliminate occupational exposure or reduce it to the lowest feasible extent" (OSHA CPL 2-2.69 § XIII, D.2.). The employer's exposure control plan is to describe the method the employer will use to meet the regulatory requirement. The plan must be reviewed and updated at least annually to reflect changes in technology that will eliminate or reduce exposure (Sec. 1910.1030(c)(1)(iv)).

In the case of currently available FNA medical devices for both EUS and EBUS, once the sample has been aspirated from the desired anatomical location, the FNA catheter is removed from the echoendoscope and handed to the cytopathologist for sample extraction/preparation. The user is instructed to "re-sheath" the needle (i.e. retract the needle into the catheter sheath) prior to detachment from the echoendoscope.

However, in many instances, this does not occur. As such, the needle sharp of the device is exposed during removal and transfer of the FNA device among medical staff in the EUS/EBUS suite with increased risk of "needle sticking" and blood borne pathogen contamination/exposure to same.

Therefore, a need exists for an improved device for use in endoscopic ultrasound procedures which address the lack of adherence to OSHA HR 5178, of current EUS and EBUS Fine Needle Aspiration devices.

Additionally, prior FNA devices in the art are not designed to individually accommodate needles of various diameters. Prior art fine needle aspiration device design used in the field of endoscopic ultrasound sample acquisition, are designed such that the sampling needle is fully integrated into the handle drive mechanism of the device. Specifically, in the case of prior art devices, the full system needle biopsy device (handle and integrated needle) must be removed from an endoscope during a procedure if a clinician chooses to utilize needles of different sizes. In this instance, the sample aspirate is removed from the needle of the device with an en-suite cytopathologist. The removal and prepping of the aspirated sample is time consuming and results in significant wait-time for the clinician between needle biopsy system passes and sampling.

Another drawback of current FNA devices known in the art is that if the same needle biopsy system (as in the case of the prior art) is used throughout a procedure for sampling at numerous anatomical locations, the durability of both the needle and the stylette components of the device frequently become compromised (i.e. the needle and/or stylette components may take a "shape-set", kink or fracture). This results in a prolonging of the procedure for the clinician, hospital staff and prolonged periods of sedation for the patient with a reduction in overall procedural efficiency.

In this instance, the clinician must remove the needle biopsy system from the endoscope; open a second new device of different needle size; re-insert the new device into the endoscope and re-confirm position of the endoscope and needle relative to the intended sampling site, before acquiring the sample. In many instances, the device may be un-useable after successive needle passes. In this instance, no alternative exists for the clinician but to utilize a new device for the remainder of the procedure.

A further drawback of prior art fine needle biopsy devices used in endoscopic and endobronchial ultrasound procedures concerns the lack of flexibility provided to the clinician during a procedure.

Current EUS-FNA needle biopsy systems are commercially available in needle sizes of 19, 22 and 25 gauge, with integrated handle and needle embodiments. In many instances the endoscopist or pulmonologist may desire to utilize a different size needle during a procedure. For example, a clinician may begin an endoscopic ultrasound or endobronchial ultrasound procedure with: (1) a device having a needle biopsy system with a diameter of 19 AWG; (2) aspirate the sample; (3) remove the needle biopsy system from the endoscope; (4) attach and lock a new needle biopsy device (for example, 22AWG size) to the endoscope and continue the procedure. This results in a loss of procedural efficiency for the clinician, patient and hospital and also increases procedural costs through the utilization of a second, new needle biopsy device.

Therefore, a need exists for an improved device for use in endoscopic ultrasound and endobronchial procedures which increases procedural efficiency, reduces procedural costs and improves procedural economics.

SUMMARY OF THE INVENTION

The invention provides a device for needle biopsy that includes a novel for a delivery handle system for interchangeably delivering needles of various sizes to a biopsy site. The delivery handle system has an adjustable length, a longitudinal axis defining a lumen extending therethrough, and includes a proximal handle member, a middle handle member and a distal handle member. The proximal handle member is slideably disposed over at least a portion of the middle handle member, the middle handle member is slideably disposed over at least a portion of the distal handle member. The proximal handle member includes an inner hub housing component having an internally cylindrical shape configured to interchangeably receive a needle subassembly that can be inserted into and withdrawn from the proximal handle member.

The needle subassembly for insertion into and withdrawal from the delivery handle system includes an aspiration needle of a plurality of different sizes, each needle having a proximal end portion and a distal end portion. Preferably, the aspiration needle ranges in size from a 15 AWG to a 28 AWG aspiration needle (e.g., 19 AWG, 22 AWG or 25AWG). A needle luer and a needle hub are coupled to the proximal end portion of the needle, the needle hub being configured for coupling with the inner hub housing component of the proximal handle member. The needle subassembly further includes a needle protector subassembly configured for coupling to the distal end portion of the needle. The needle protector subassembly includes a needle protection hub having a lumen extending therethrough configured for receiving the distal end portion of the needle, a deformable O-ring axially disposed within the lumen of the needle protection hub, and a tubular sheath defining a lumen extending from a distal end of the needle protection hub. The lumen of the tubular sheath is in communication with the lumen of the needle protection hub for receiving the needle when inserted into the needle protection hub. In one embodiment of the invention, the tubular sheath distally extending from the needle protector subassembly includes an internally tapering distal end.

In a preferred embodiment, the aspiration needle of the needle subassembly includes a collet surrounding the distal end portion of the needle. The collet has a diameter larger than the diameter of the deformable O-ring of the needle protection hub, such that the collet traverses the deformable O-ring when the needle is inserted into or withdrawn from the lumen of the needle protection hub, thereby locking the needle protector subassembly onto the distal end portion of the needle during insertion and withdrawal of the needle subassembly from the delivery handle system. The collet preferably chamfered at the proximal and distal ends to provide a smooth interface with the needle protector subassembly during needle exchange.

The aspiration needle of the needle subassembly also preferably includes a distal tip having four distinct angular bevel grinds, including a primary angle relative to the needle shaft, a secondary angle relative to the needle shaft, and a back-cut angle relative to the secondary angle for providing a smooth needle passage during needle insertion and withdrawal during a biopsy procedure.

The lumen extending through the delivery handle system includes an inner hypotube component at least partially disposed within the proximal handle member and an outer hypotube component disposed at least partially within the middle handle member. The inner hypotube is coupled to the outer hypotube and configured to longitudinally slide within the outer hypotube when the proximal handle member is distally advanced or proximally retracted over the middle handle member. The lumen further includes a tubular catheter sheath coupled to a distal end of the outer hypotube. The inner hypotube, outer hypotube and catheter sheath are in constant communication with each other.

Preferably, the catheter sheath includes a helically braided reinforcement structure and has an outer diameter ranging from 0.05 inches to 0.140 inches, and an inner diameter ranging from 0.05 inches to 0.120 inches. In certain embodiments, the catheter sheath includes a tapered distal tip having an outer and inner diameter that is smaller than the outer and inner diameters of the remaining length of the catheter sheath. In certain embodiments, the inner diameter of the distal tip ranges from 0.020 inches to 0.060 inches.

The delivery handle system of the invention further includes an inner handle member disposed within an inner portion of the middle handle member. The inner handle member is coupled to a proximal portion of the catheter sheath and a distal portion of the outer hypotube, such that the catheter sheath is distally extended into the distal handle member when the middle handle member is distally advanced over the distal handle member.

The delivery handle system of the invention further includes a first locking mechanism configured to prevent the proximal handle member from longitudinally sliding over the middle handle member, and a second locking mechanism configured to prevent the middle handle member from longitudinally sliding over the distal handle member. The first locking mechanism includes a first ring slideably disposed around at least a portion of the middle handle member. A screw is threaded within the first ring for locking the first ring in a fixed position along the middle handle member. The second locking mechanism includes a threaded insert disposed along a distal portion of the middle handle member. The threaded insert is coupled to a screw for tightening the threaded insert to lock middle handle member in a fixed position along the distal handle member.

The proximal handle member of the delivery handle system of the invention includes an inner retention collar disposed at a distal end of the inner hub housing component. The inner retention collar is configured to receive the needle protection hub coupled to the needle. At least a portion of the retention collar is recessed, and the deformable O-ring component is disposed within the recessed portion for securing the needle protection hub within the retention collar upon insertion of the needle subassembly into the proximal handle member.

In certain embodiments, the O-ring of the retention collar has a diameter smaller than a diameter of the needle protection hub, such that the needle protection hub traverses the deformable retention collar O-ring when the needle subassembly is inserted into or withdrawn from the proximal handle member thereby locking the needle protector subassembly onto the proximal handle portion during insertion and withdrawal of the needle subassembly from delivery handle system.

The proximal handle member further includes a locking mechanism for releasably locking the needle hub within the inner hub housing component of the proximal handle member. The locking mechanism includes a depressible latch component securely coupled to the proximal handle member. The latch includes a deflectable hinge coupled to a barb component, that is coupled to the inner hub housing component and disposed within an interior portion of the proximal handle member.

The needle hub of the needle subassembly includes an internal land ring for interacting with the deflectable hinge and barb component of the locking mechanism. The internal land ring traverses the deflectable hinge of the latch component when the needle subassembly is inserted into the lumen of the proximal handle member, thereby causing the deflectable hinge to deflect against the barb component during insertion. The deflectable hinge returns to a home position once the internal land ring has cleared the deflectable hinge to prevent the needle hub from moving backwards. The needle subassembly is released from the inner hub housing component of the proximal handle member by depressing the latching component to cause the deflectable hinge to deflect against the barb component to allow the internal land ring to clear the deflectable hinge and barb.

In certain embodiments, the inner hub housing component of the proximal handle member includes a plurality of depressions spaced around an internal circumference of the hub housing component and the needle hub comprises a plurality of protrusions. The plurality of depressions are configured to receive the plurality of protrusions to prevent the needle hub from rotating relative to the hub housing component. Alternatively, the inner hub housing component includes a smooth internal circumference and the needle hub comprises a smooth outer surface to allow the needle hub rotate relative to the hub housing component.

In certain embodiments, the delivery handle system of the invention includes a luer holder coupled to a distal end of the distal handle member for coupling the distal handle member to a working channel port of an endoscope. In such embodiments, the luer holder includes a luer lock for locking the distal handle member in a fixed position relative to the working channel of the endoscope to prevent the delivery handle system from rotating about the working channel.

These and other aspects of the invention are described in further detail in the figures, description, and claims that follow.

BRIEF DESCRIPTION OF DRAWINGS

In the following description, various embodiments of the present invention are described with reference to the following drawings that illustrate exemplary embodiments of the invention. Together with the description, the drawings serve to explain the principles of the invention. In the drawings, like structures are referred to by like numerals throughout the several views. Note that the illustrations in the figures are representative only, and are not drawn to scale, the emphasis having instead been generally placed upon illustrating the principles of the invention and the disclosed embodiments.

FIG. 2 is a drawing of the aspiration needle sub-assembly of the present invention.

FIG. 3 is a cross sectional drawing of the needle protector embodiment of the present invention shown in FIG. 2.

FIG. 4 is a cross sectional drawing of the proximal end of the aspiration needle sub-assembly shown in FIG. 2

FIG. 4A is a drawing of an alternate preferred embodiment of the proximal end of the aspiration needle sub-assembly with strain relief;

FIG. 4B is a cross sectional drawing of the proximal end of the aspiration needle sub-assembly with strain relief.

FIG. 6 is an enlarged view of encircled Portion A shown in FIG. 5, and depicts a cross sectional drawing of the needle locking mechanism of the delivery system handle of the present invention.

FIG. 7 is an enlarged view of encircled Portion B shown in FIG. 5, and depicts cross sectional drawing of the needle extension length adjustment mechanism of the delivery system handle of the present invention.

FIG. 11 is a drawing of the extreme distal end of the needle.

FIG. 12 is a drawing of the bevel detail of the needle of the present invention, incorporating primary angle, secondary angle, tertiary and back-cut angle elements.

FIG. 13 is a cross sectional drawing of the bevel detail of the needle of the present invention, illustrating the tertiary angle of the grind detail.

FIG. 19 is a cross-sectional drawing of locking functionality between the needle hub, thumb latch and hub housing components.

DETAILED DESCRIPTION

The invention provides a device for needle biopsy for collecting tissue, fluid, and cell samples in conjunction with procedures such as an endoscopic ultrasound (EUS) or endoscopic bronchial ultrasound (EBUS).

Figure 1:
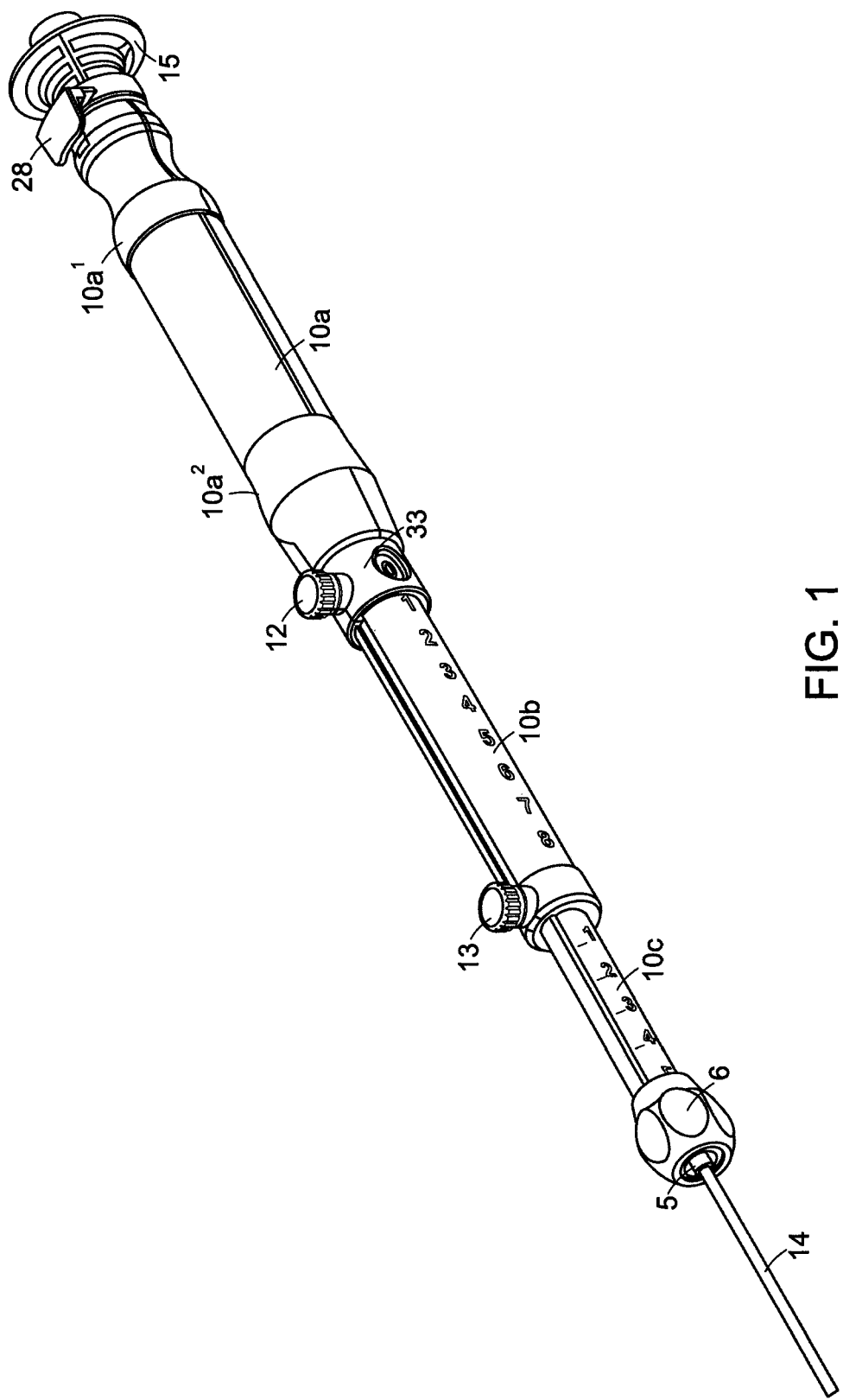
FIG. 1 is an assembly drawing depicting the present invention incorporating the delivery system handle, catheter sheath and aspiration needle for the intended field of use.

An exemplary embodiment of the proposed device assembly is illustrated in FIG. 1. The device design consists of a handle mechanism (delivery system handle 10) and aspiration needle sub-assembly 15. The delivery system handle 10 includes a proximal handle member 10a, a middle handle member 10b, and a distal handle member 10c. The proximal, middle and distal handle members each include an inner lumen and are coupled together to define a longitudinal axis such that the inner lumens are in constant communication and extends throughout the length of the coupled handle members. Proximal handle member 10a is slideably disposed over at least a portion of the middle handle member 10b, and middle handle member 10b is slideably disposed over at least a portion of distal handle member 10c. The proximal handle member 10a includes proximal handle grip $10a^1$ a distal handle grip $10a^2$. The delivery handle system 10 further includes an inner handle member 10d disposed within the inner lumen of the middle handle member 10b (shown in FIGS. 5 and 7). The delivery system handle 10 also incorporates a catheter sheath 14 component coupled to the distal end of the distal handle member 10c. This component provides a conduit between the delivery system handle 10 and the target sampling site during the exchange of aspiration needles. The device design is modular in that the needle sub-assembly 15 can be detached from the proximal handle 10a of the device for each individual "pass" or aspirated sample taken by the endoscopist at the site of the lesion or abnormality.

The delivery system handle 10 incorporates two length adjustment features actuated via adjustment of two thumbscrew locking mechanisms. A threaded proximal thumbscrew 12 and locking ring 33 are moveably disposed around the middle handle member 10b; the proximal thumbscrew 12 is loosened to loosen locking ring 33, locking ring 33 is moved distally along the middle handle member 10b and tightened in the desired position along middle handle member 10b via proximal thumbscrew 12 to allow the user to establish a set depth of needle penetration beyond the end of the catheter sheath 14. A threaded distal thumbscrew 13 is transversely disposed at the distal portion of the middle handle member 10b; the distal thumbscrew 13 is loosened to move the middle handle member 10b distally and/or proximally and tightened to allow the user to establish a set depth of catheter sheath 14 extension beyond the end of the endoscope.

The needle sub-assembly 15 consists of the needle shaft 21(which can range in length from 500 mm up to 2500 mm, but which more preferably ranges in length between 1640 mm to 1680 mm) and is beveled at the distal needle end to enhance tissue penetration during sample acquisition; needle hub 17; needle luer 18; needle collet 19; needle protector sub-assembly 9; stylette hub 20 and stylette shaft 22. The needle component itself can be manufactured from a number of metallic based (Stainless steel or alloys thereof; Nitinol or Alloys thereof etc . . . ) or Polymeric Based materials including, but not limited to Poly-ether-ether ketone, Polyamide, Poyethersulfone, Polyurethane, Ether block amide copolymers, Polyacetal, Polytetrafluoroethylene and/or derivatives thereof).

FIG. 2 illustrates the aspiration needle sub-assembly 15 of the present invention. This sub-assembly is inserted into and removed from the lumen of the delivery system handle 10 in acquiring tissue samples. The sub-assembly 15 consists of a stylette hub 20 and stylette shaft 22 components which are securely locked on the needle luer 18 of the aspiration needle via conventional internal luer threads (as is know to persons skilled in the art). The stylette hub 20 may be attached to the stylette shaft 22 via a number of processing techniques such as adhesive bonding or insert injection molding. The female luer of the aspiration needle incorporates a mating luer thread detail, onto which the stylette hub 20 may be tightened. The needle luer 18 element of the present invention may be attached to the proximal end of the needle shaft via a number of processing techniques such as adhesive bonding or insert injection molding.

The aspiration needle sub-assembly 15 also incorporates a needle collet 19 (previously described as "needle protrusion(s) and shown in FIGS. 3 and 10 of Applicant's co-pending application (U.S. Ser. No. 12/243,367, published as US2010/0081965). The function of this needle collet 19 is to (1) provide a means to center the needle shaft component in the catheter sheath of the delivery system during needle exchange (2) provide a mechanism or securing and locking the needle protector sub-assembly to the distal end of the aspiration needle once the needle has been unlocked and withdrawn from the delivery system handle. The needle collet 19 of the present invention may be attached to the distal end of the needle shaft 21 via a number of processing techniques such as adhesive bonding, laser welding, resistance welding, or insert injection molding. The needle collet 19 may be fabricated from metals materials such as stainless steel, nickel titanium or alloys thereof or polymer materials such as, but not limited to, Polyacetal, polyamide, poly-ether-block-amide, polystyrene, Acrylonitrile butadiene styrene or derivatives thereof. The needle collet 19 is located at a set point distance from the extreme distal end of the beveled needle. The distance from the extreme distal end of the needle bevel to the proximal collet position on the needle may be within the range of 6 cm to 12 cm but is more preferably in the range of 7 cm to 9 cm and ore preferably is located 8 cm from the end of the needle. This ensures that when the needle is extended to it's maximum extension distance relative to the distal end of the catheter sheath (i.e. 8 cm), the collet 19 does not exit the end of catheter sheath 14.

Figure 14:
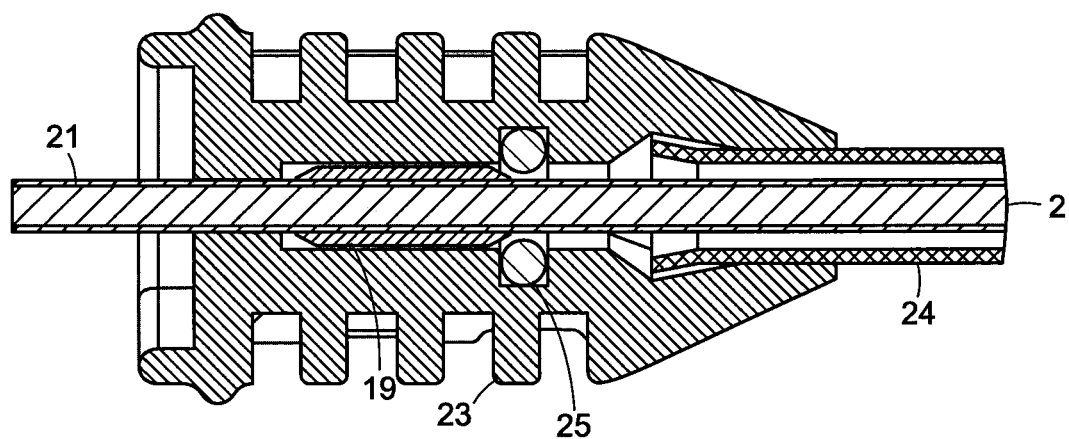
FIG. 14 is a cross sectional drawing of the proximal end of the needle protector hub sub-assembly.

FIGS. 3 and 14 illustrate the needle protection sub-assembly 9 design embodiment of the current invention, in the locked position at the distal end of the needle. The needle protection sub-assembly 9 consists of two needle protector (NP) hub halves (collectively 23), which are adhesively bonded to each other, on the proximal end of the needle protector (NP) sheath component 24. Alternately, these NP hub halves 23 may be snap fit together or may be insert injection molded over the NP sheath 24 to provide a secure bond/attachment between these components in the assembly. The needle protection sub-assembly 9 also incorporates a needle protector (NP) hub O-Ring component 25. This component resides in a recessed cut-out in the center of the assembled NP hub halves 23. This NP hub O-Ring 25, in conjunction with the needle collet 19 which is securely attached to the distal end of the needle shaft 21 of the sub-assembly 9, provides a mechanism for locking the NP sub-assembly 9 onto the end of the needle. In this way, the bevel of the needle is protected, covered and shielded once the needle has been removed from the delivery system handle. It is desired that the NP sheath 24 of the present invention be manufactured from a translucent polymer such as, but not limited to polyurethane, polyamide and derivatives thereof.

The needle hub 17 embodiment of the aspiration needle sub-assembly as shown in FIG. 2 and FIG. 4 of the present invention, provides a mechanism which (1) locks the aspiration needle sub-assembly 15 into the delivery system handle 10 by means of the hub housing 27 and thumb latch 28 components (as will be described later in this disclosure) and (2) provides a means to lock the needle protection sub-assembly 9 embodiment shown in FIG. 3, into the delivery system device handle 10, as will be described later. As shown in FIG. 4, the needle hub component 17 is securely attached to the needle luer 18 and needle shaft 21 components of the aspiration needle sub-assembly 15. The needle hub element 17 of the present invention may be attached to the distal end of the needle luer component 18 via a number of processing techniques such as adhesive bonding or insert injection molding.

An alternate preferred embodiment of the proximal end of the aspiration needle sub-assembly 15 is shown in FIGS. 4A and 4B. This embodiment incorporates a strain relief component 26, which extends from the distal end of the needle luer component 18, through the body of the needle hub component 17, to extend beyond the distal end of the needle hub 17. This tubular strain relief component 26 is intended to provide a more gradual stiffness transition between the needle hub 17 and needle shaft 21 components, particularly in the case of smaller needle gauge sizes (such as 22A WG and 25A WG). This strain relief component 26 may range in length from 10 mm to 50 mm but is more preferably in the range of 25 mm to 35 mm. The diameter of this strain relief component 26 must be sufficiently small so that it fits through the proximal end of the needle protection sub-assembly 9 (as shown in FIG. 3) and does not impair the ability for the NP sub-assembly 9 to slide back and forth on same. This strain relief component 26 may range in outer diameter from 0.020 inches to 0.060 inches but is more preferably in the range of 0.026 inches to 0.045 inches. This tubular strain relief 26 may be fabricated from metal based materials, such as but not limited to stainless steel, nickel titanium or alloys thereof or polymer materials such as, but not limited to, Polyacetal, polyamide, poly-ether-block-amide, polystyrene, Acrylonitrile butadiene styrene or derivatives thereof.

Figure 5A:
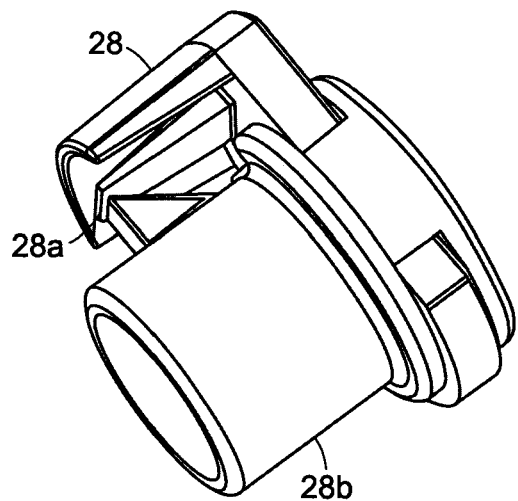
FIGS. 5A through 5D depict various enlarged views of a thumb latch component included in the proximal portion of the delivery system handle of the invention.
Figure 5B:
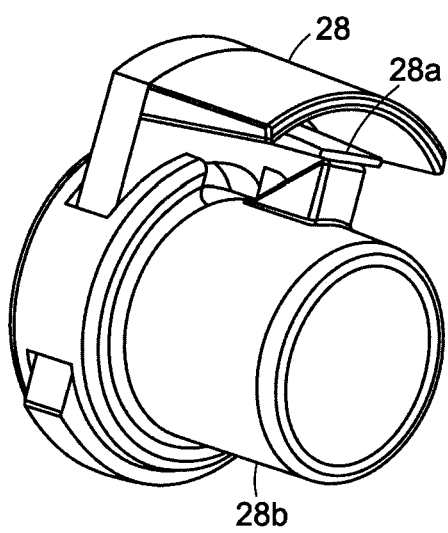
Figure 5C:
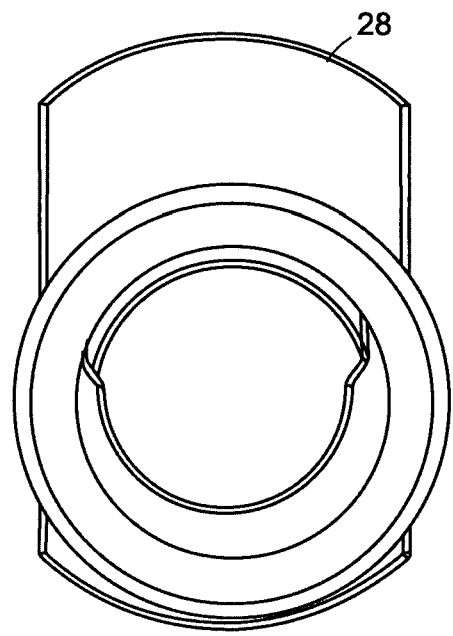
Figure 5D:
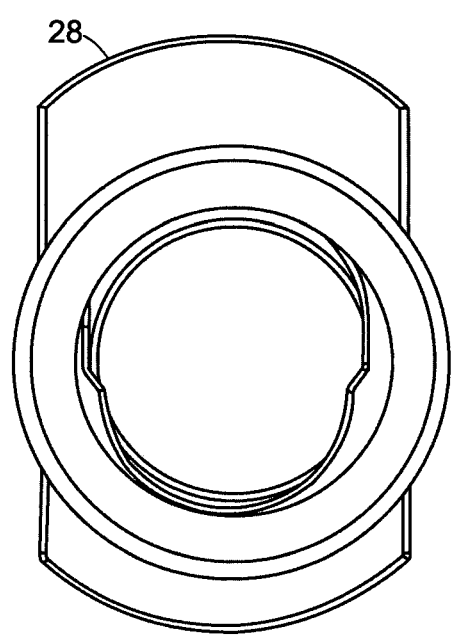
Figure 5:
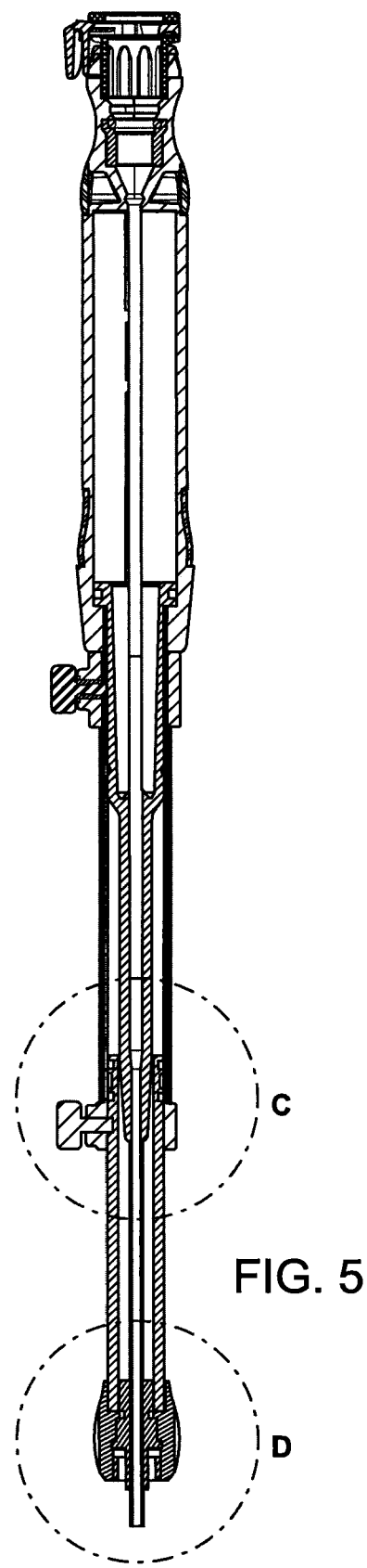
FIG. 5 is a cross sectional drawing of the delivery system handle of the present invention.

FIG. 5 is a sectional view of the delivery system handle 10 for the present invention, without the aspiration needle sub-assembly 15 loaded therein. FIG. 6 (Detail A from FIG. 5) illustrates a sectional view of the proximal end 10a of the assembled device handle. This proximal portion of the handle (also shown in FIG. 16 and FIG. 18) contains elements to ensure secure, yet releasable locking of the aspiration needle sub-assembly 15 in the delivery system handle 10. The hub housing component 27 is secured to the proximal delivery system handle halves 10a via adhesive bonding or ultrasonic welding techniques. The thumb latch component 28 is securely locked into the hub housing component 27 via a one-way keying action. Once the thumb latch component 28 is inserted into the hub housing component 27, the thumb latch 28 cannot be disassembled and may only be moved in the transverse direction to actuate the assembled mechanism.

FIGS. 5A, 5B, 5C, and 5D depict various views of an exemplary embodiment of the thumb latch component 28 of the delivery system handle 10. The thumb latch component 28 represents a mechanism to releasably lock the needle hub 17 of aspiration needle sub-assembly 15 within the hub housing 27 of the proximal handle member 10a of the delivery device. Thumb latch 28 may be, for example, a push-button, that activates the use of a deflectable hinge member 28a to provide for a return to the "home" position once external force is not applied to release thumb latch 28. Hinge member 28a can elastically deform to provide for the opening and closing of the "lock" during removal of the aspiration needle sub-assembly 15 from the delivery system handle 10. In one embodiment, thumb latch 28 incorporates an external coupler housing 28b and a push button design mechanism. FIGS. 5C and 5D illustrates thumb latch 28 in the CLOSED and OPEN positions during a typical actuation cycle.

Referring to FIGS. 5A and 5B, thumb latch 28 and external coupler housing 28b may be manufactured from a range of rigid, non-deformable, thermoplastic or thermoset materials such as, acrylonitrile butadiene styrene (ABS), styrene acrylonitrile (SAN), polystyrene or rigid derivatives thereof, polyamide, polyethylene, polyurethane, and polycarbonate. In an embodiment, the materials of manufacture have a durometer in the range of 35-120 Shore D, but more preferably in the range of 80-110 Shore D.

Hinge member 28a may be manufactured from a range of rigid, thermoplastic or thermoset materials such as, acrylonitrile butadiene styrene (ABS), styrene acrylonitrile (SAN), polystyrene or rigid derivatives thereof, polyamide, polyethylene, polyurethane, and polycarbonate. In an embodiment, the materials of manufacture shall be capable of deformation in bending under the application of an applied load, such as is encountered during a typical "Open and Close" cycle for the needle biopsy device without crazing, fatigue or cracking.

The proximal portion of the proximal handle member 10a of the delivery system handle 10, incorporates a retention collar 29 and a retention collar O-ring component 30. The retention collar component 29 resides in a cut out nest in the proximal handle half, and is in communication with inner hub housing component 27. The retention collar 29 is a cylindrical component, which is internally tapered and recessed to provide an internal, recessed shelf. The retention collar O-ring component 30 resides in this recessed shelf and is secured in position through the assembly of both halves of the delivery system handle halves. The purpose of this retention O-Ring component 30 is to provide a method to lock and maintain the needle protector hub sub-assembly 9 of the aspiration needle sub-assembly 15, securely in the handle 10 of the delivery system while the tissue sample site is being accessed by the clinician, as described in detail below. The functionality and operation of this retention collar O-Ring component 30 is the same as described in FIGS. 41 and 42 and associated abstract of the specification of Applicant's co-pending patent application U.S. Ser. No. 12/607,636 (published as US2010/0121218).

As shown in FIG. 6, the delivery system handle assembly 10 of the present invention incorporates an inner hypotube component 31. It is the design intent of this component to provide a conduit between the proximal handle member 10a of the delivery system, and the outer hypotube component 32 shown in FIG. 7. The inner hypotube component 31 may be fabricated from metal based materials, such as but not limited to stainless steel, nickel titanium or alloys thereof or polymer materials such as, but not limited to, Polyacetal, polyamide, poly-ether-block-amide, polystyrene, Acrylonitrile butadiene styrene or derivatives thereof. The inner hypotube 31 is secured to the assembled handle halves of the device via adhesive bonding or insert injection molding techniques. During needle advancement, the proximal handle member 10a of the delivery system is distally advanced, in order to advance the distal end of the needle into the desired tissue sampling site. When the proximal handle member 10a is distally advanced, the inner hypotube 31 is also advanced in unison in a distal direction. The inner hypotube component 31 is in constant longitudinal communication with the outer hypotube component 32 and is designed to telescope inside the outer hypotube component 32 at all times. This ensures that needle passage during needle exchange into and out of the delivery system, is not impaired.

Referring now to FIG. 7 (Detail B from FIG. 5), a cross sectional view of the distal end of the proximal handle member 10a and the middle handle member 10b is illustrated. During a typical EUS FNA procedure, the locking ring component 33 is loosened via proximal thumbscrew 12, moved distally and set to a pre-established depth by the clinician, dependent upon depth of needle penetration required. Once the locking ring 33 has been moved distally (via the proximal thumbscrew) and locked to the required depth of penetration, the proximal handle member 10a of the delivery system is advanced. During advancement, the proximal handle member 10a moves in a longitudinal direction over the middle handle member 10b and inner handle member assembly 10d. The inner handle member 10d and middle handle member 10b components are securely bonded to each via adhesive bonding or ultrasonic welding techniques and remain in a stationary, locked position during needle advancement via proximal handle 10a actuation in a distal direction.

As shown in FIG. 7, the outer hypotube component 32 is also in constant communication with the catheter shaft component 14 of the delivery system. The proximal end of the catheter shaft component 14 is flared in an outward direction. The distal end of the outer hypotube component 32 is inserted into flared end of the catheter shaft 14 and secured thereto via adhesive bonding or insert injection molding techniques. The inner handle member 10d is bonded to both the proximal end of the catheter shaft 14/outer hypotube 32 assembly via adhesive bonding or insert injection molding techniques. In this way, the inner hypotube 31, outer hypotube 32 and catheter sheath 14 are in constant communication, ensuring for smooth needle passage during needle exchange. This design embodiment, also ensures that the catheter sheath 14 my be advanced through the distal handle member 10c as required.

Figure 8:
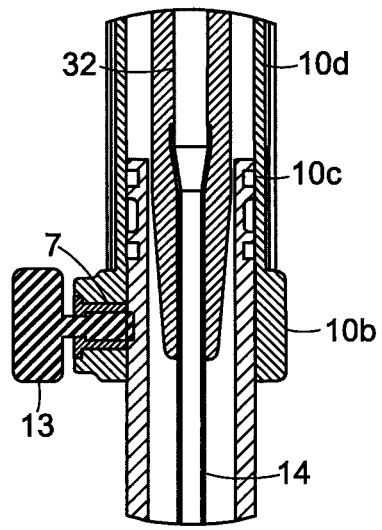
FIG. 8 is an enlarged view of encircled Portion C shown in FIG. 5, and depicts a cross sectional drawing of the catheter sheath extension length adjustment mechanism of the delivery system handle of the present invention.
Figure 9:
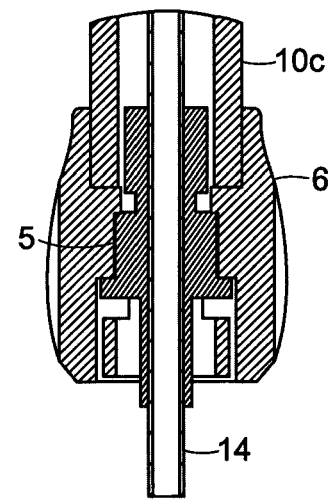
FIG. 9 is an enlarged view of encircled Portion D shown in FIG. 5, and depicts a cross sectional drawing of the distal end of the assembled delivery system handle of the present invention, incorporating the mechanism for attachment to the endoscope.

FIGS. 8 and 9 illustrate the design assembly embodiments for catheter sheath extension length adjustment in the case of the present invention. Referring to FIG. 8, the distal end of the middle handle member 10b incorporates a threaded insert 7 and distal thumbscrew 13. The catheter sheath extension distance beyond the end of the endoscope may be adjusted by loosening the distal thumbscrew 13 and advancing the middle handle member 10b in a distal direction over the distal handle member 10c. The distal handle member 10c and middle handle member 10b are in constant longitudinal communication with each other.

Referring to FIG. 9, the distal end of the delivery system handle assembly 10 is illustrated. The distal handle member 10c is secured to a recess in the distal luer holder 6 via adhesive bonding or ultrasonic welding techniques. The distal luer holder component 6 is securely attached to the scope luer lock component 5 via adhesive bonding or insert injection molding techniques. The distal handle member 10c is designed in such a way that once the device handle is attached to the working channel port of the endoscope, the assembly cannot rotate independently of assembled scope luer lock 5 and distal luer holder 6 components. Once the entire delivery system handle 10 (as shown in FIG. 1 and cross sectional view FIG. 5) has been locked onto the endoscope via the scope luer lock 5, the catheter sheath length and needle penetration extension length may be established as previously described.

FIG. 10 is an illustration of the distal end of the aspiration needle of the present invention, with needle collet (referred to as "needle protrusions" in Applicant's co-pending patent application U.S. Ser. No. 12/607,636, published as US2010/0121218) secured on the needle. It is preferable that the length of this needle collet 19 be in the range of 2 mm to 10 mm, but more preferably in the range of 3.5 mm to 5 mm. It is preferable that the outer diameter of the needle collet 19 be in the range of 0.030 inches to 0.080 inches, but more preferably in the range of 0.040 inches to 0.070 inches. This needle collet component 19 (see also FIG. 14 and FIG. 26) is also chamfered at the proximal and distal ends of same. It is preferable that the chamfer angle of the needle collet be in the range of 15 degrees to 80 degrees, but more preferably in the range of 30 degrees to 60 degrees. This chamfer on both ends of the needle collet 19 is intended to provide smooth locking and unlocking with the needle protector sub-assembly 9 during needle exchanges.

Figure 10A:
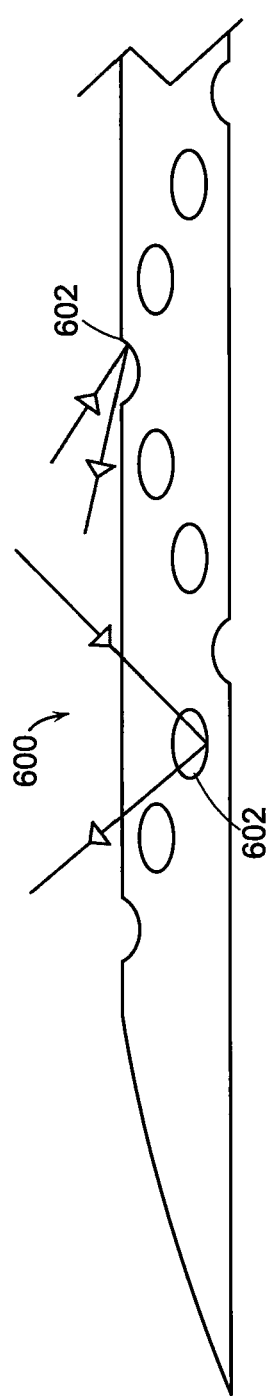
FIGS. 10A through 10O depict exemplary embodiments of an echogenically enhanced region at the distal end of an aspiration needle for use in the devices of the invention.

As depicted in FIG. 10, and FIGS. 10A through 10O, the distal end of the needle of the present invention incorporates an embodiment to enhance the echogenic signature of the needle. In the case of the present invention, this echogenically enhanced region 34 can be fabricated by, but not limited to roughening the end of the needle over a predefined length close to proximal end of the needle bevel 35. It is preferable that the length of this echogenically enhanced region 34 be in the range of 2 mm to 20 mm, but is more preferably in the range of 10 mm to 15 mm. In the case of the present invention, the echogenic enhanced pattern is imparted to the needle via a micro-blasting process which roughens the surface of the needle over a specific length, improving the visibility of the needle under endoscopic ultrasound.

In certain aspects of the invention, the echogenically enhanced region of the needle is achieved through the removal of material from the surface of the needle to provide greater reflectivity and strengthened reflected signal. It is contemplated that the removal of material does not, however, reduce the performance of the needle from a pushability perspective or deter its ability to acquire a desired sample.

Figure 10D:
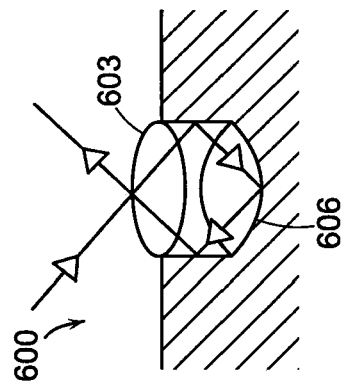
FIG. 10 is a drawing of the distal end of the needle with mounted needle collet.
Figure 10C:
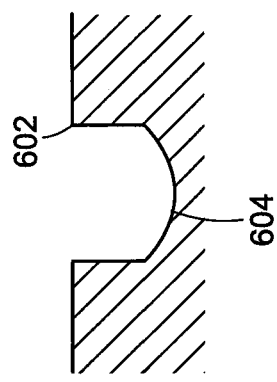
Figure 10B:
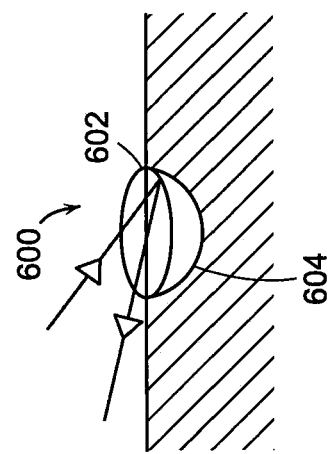
Figure 10E:
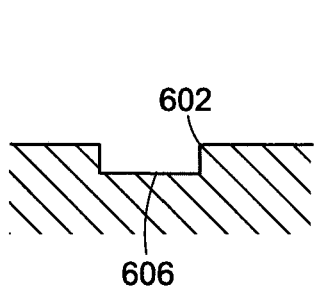
Figure 10F:
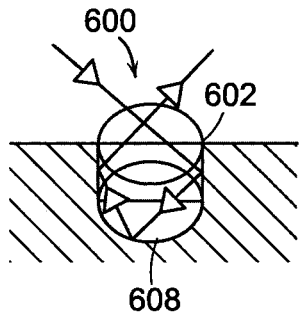
Figure 10G:
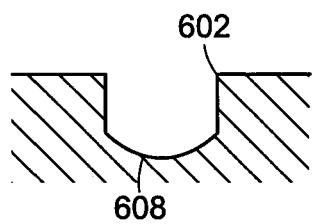

Referring now to FIG. 10A, a perspective view of an embodiment of a needle 600 is presented. Needle 600 is comprised of a plurality of depressions 602. Depressions 602 may be, but are not limited to, circular, concave, cylindrical, helical, oval, rectangular, and square elements that take the form of indentations on the surface of needle 600. Depressions 602 may be arranged in a helical (spiral) fashion around the circumference of the distal needle end. These indentations may extend to the extreme end of the bevel or may end at a specific distance from the bevel of needle 600. The length of the distal end of needle 600 containing these depressions may be, for example, from one to twenty centimeters. In another embodiment, the length is between five to ten centimeters. Referring to FIGS. 10B and 10C, depression 602 have a concave detail 604. Referring to FIGS. 10D and 10E, depressions 602 have a square base edge 606. Referring to FIGS. 20F and 20G, depressions 602 have a hemispherical base detail 608.

Figure 10H:
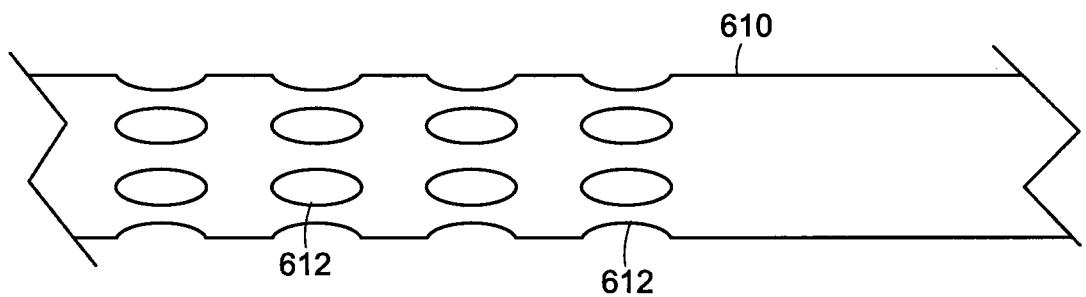
Figure 10I:
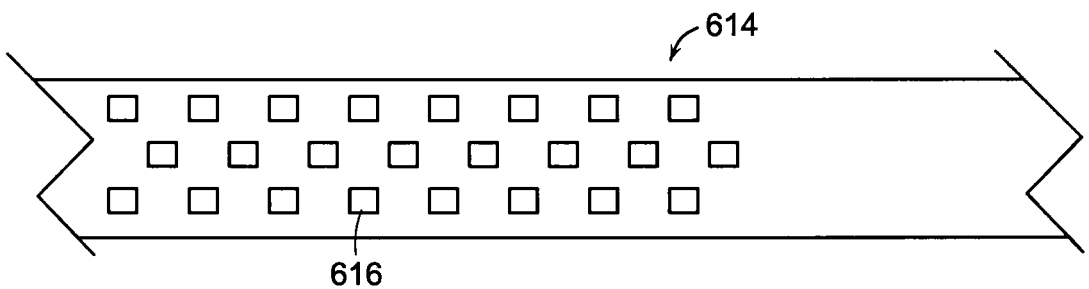
Figure 10J:
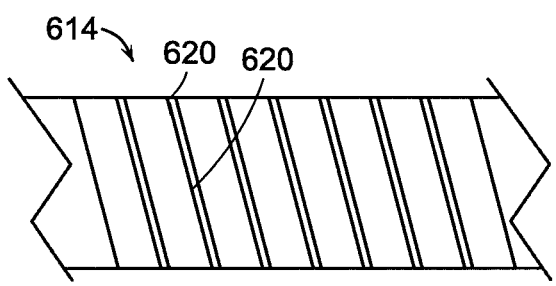
Figure 10K:
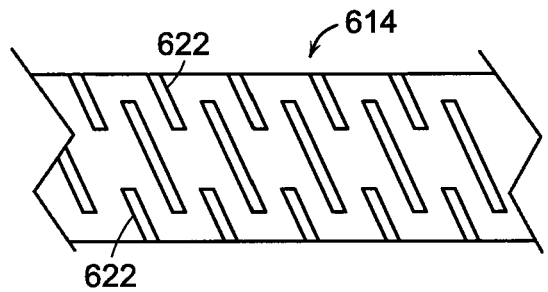

Referring now to FIG. 10H, a perspective view of another embodiment of a needle 610 is presented. Needle 610 is comprised of elliptical depressions 612 around the circumference of the distal end of needle 610. Referring to FIG. 10I, a perspective view of an embodiment of a needle 614 having square depressions 616 is presented. Depressions 616 may extend to the extreme end of the bevel or may end at a specific distance from the bevel of needle 614. Referring to FIGS. 10J and 10K, embodiments of needle 614 including spiral depressions 620 and helical depressions 622 are presented. Referring to FIG. 10L, a depression 624 has a concave detail. Referring to FIG. 10M, a depression 626 has a square base edge. Referring to FIG. 10N, a depression 628 has a hemispherical base detail.

Referring now to FIG. 10O, a diagram of ultrasound waves impinging upon a needle depression at angles of $\alpha 1$ 630 and $\beta 1$ 632 respectively are presented. In an embodiment, a wave strikes the base of the depression and is reflected upwards at angle of reflection of $\alpha 2$ 634 and $\beta 2$ 636 respectively, which are equal to the angles of incidence of $\alpha 1$ 630 and $\beta 1$ 632 respectively. This reflected beam is reflected a second time off the adjacent wall of the depression at an angle of reflection of $\alpha 3$ 638 and $\beta 3$ 640 respectively, which are equal to the angles of incidence, $\alpha 1$ 630 and $\beta 1$ 632 respectively and the angles of first reflection $\alpha 2$ 634 and $\beta 2$ 636 respectively. In this manner, the reflected wave becomes reflected along the same angle of incidence as the initially propagated incident beam back to the transducer of the ultrasound device. In an embodiment, a square edge depression design may provide for more efficient remittance of ultrasound waves during the procedure.

FIGS. 11 and 12 are drawings of the distal end of the needle of the current invention. The distal end of the needle 35 of the current invention is beveled to enhance the ability of the needle to penetrate tissue during sample acquisition. The bevel detail 35 of the present invention incorporates four angular bevel grinds, which, in addition to enhancing tissue penetration, also ensure the smooth passage of the needle down the catheter sheath of the delivery system during needle exchange. Referring to FIG. 12, the needle bevel grind of the current embodiment incorporates a primary angle ("A"), a secondary angle ("B"), a back-cut angle ("C") and tertiary angles ("D"), as shown in FIG. 13. It is preferable that the primary angle be in the range of 10 degrees to 25 degrees, but more preferably in the range of 12 degrees to 18 degrees. It is preferable that the secondary angle be in the range of 15 degrees to 35 degrees, but more preferably in the range of 22 degrees to 28 degrees. It is preferable that the tertiary angle be in the range of 15 degrees to 35 degrees, but more preferably in the range of 22 degrees to 28 degrees. It is preferable that the back-cut angle be in the range of 15 degrees to 70 degrees, but more preferably in the range of 25 degrees to 45 degrees.

During needle exchange, it is important that the aspiration needle (with pre-loaded stylette 2) can be passed through the internal diameter of the catheter sheath 14 without catching on the internal wall of same. In order to achieve this, the bevel grind of the current invention incorporates a back-cut grind detail. This back-cut detail acts as a "bumper" during needle passage through the sheath. As the needle advances, the heel of the back-cut comes in contact with the internal diameter of the sheath and reduces the friction between needle end 35 and catheter sheath 14 components. In this way, the needle can be smoothly tracked through the catheter sheath to exit the end of the catheter sheath 14.

Figure 15:
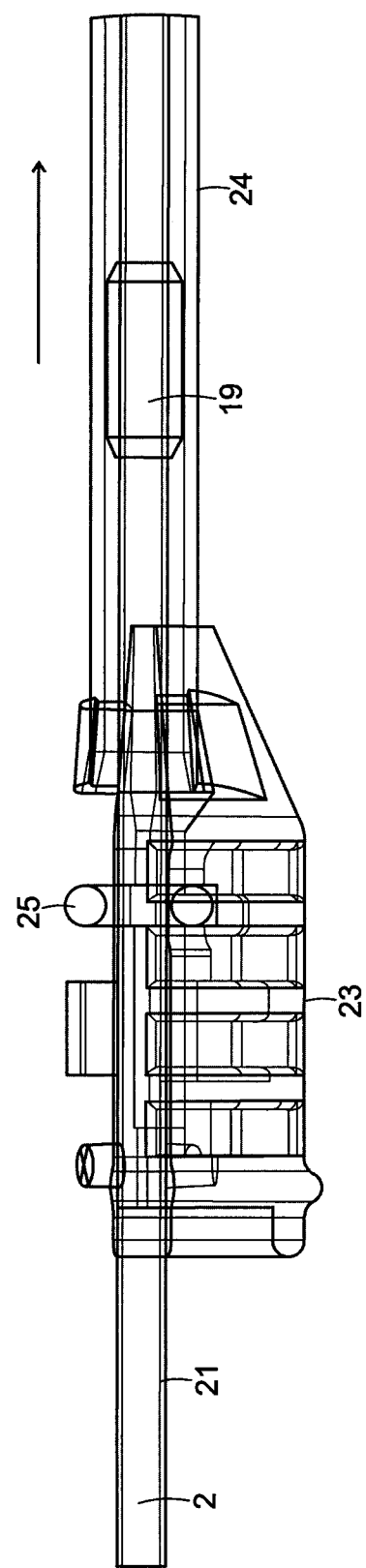
FIG. 15 is a drawing of the intended functionality of the needle protector assembly.

FIG. 14 and FIG. 15 illustrate the method of engagement and disengagement between the aspiration needle sub-assembly 15 with mounted collet 19 and the needle protector ("NP") sub-assembly 9. Referring to FIG. 14, the NP hub 23 is locked onto the needle collet 19 at the distal end of the needle shaft 21 by inserting the shaft 21 into the NP hub 23. As the needle/NP protector assembly is inserted into the handle of the delivery system, the needle 21 and needle collet 19 are advanced such that the needle collet 19 traverses the deformable NP Hub O-Ring 25. The internal diameter of the NP Hub O-Ring 25 in the non-deformed state, is smaller than the outer diameter of the needle collet

Figure 23:
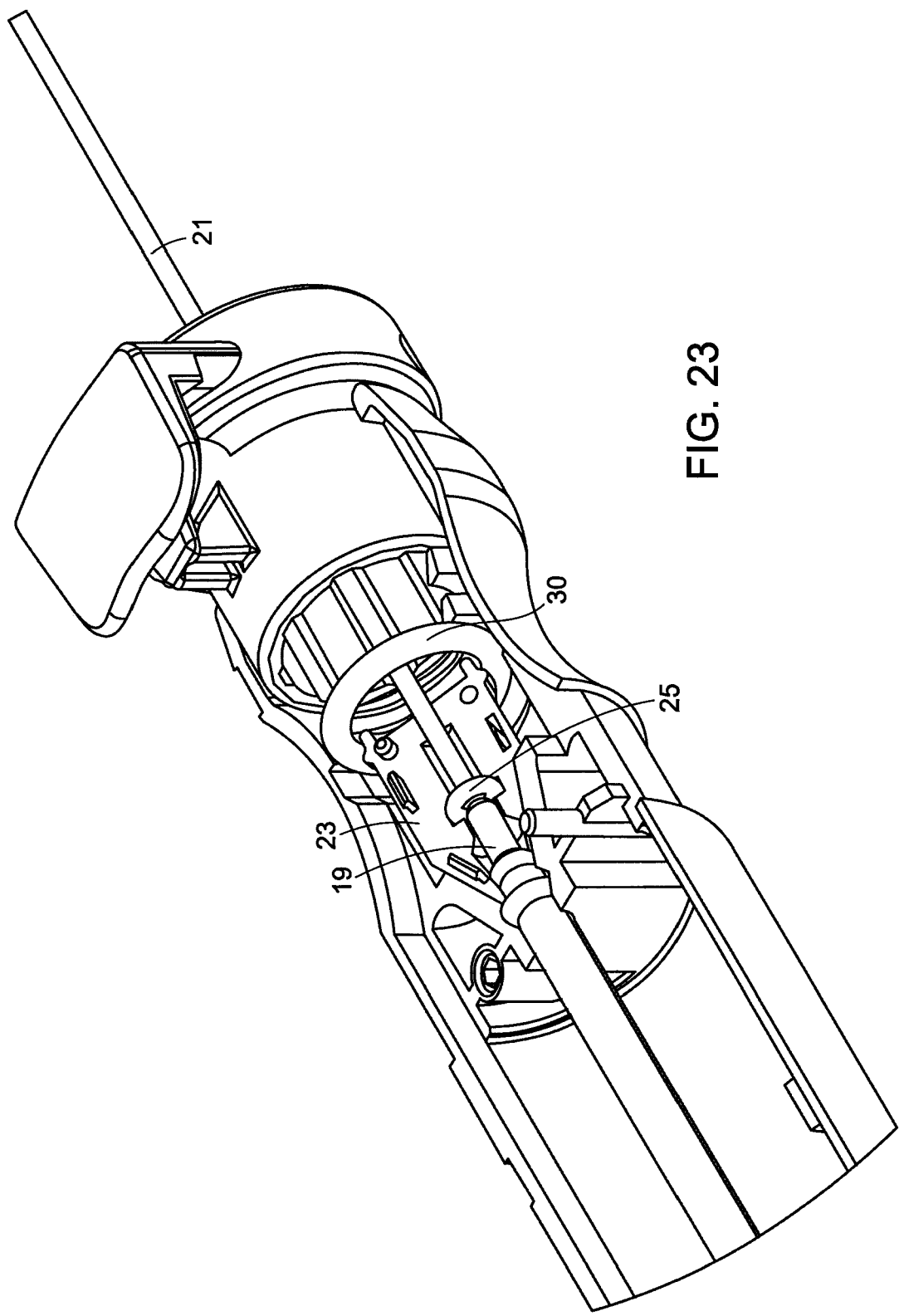
FIG. 23 is a drawing of the intended functionality of the needle collet during needle exchange and more specifically, during needle extraction from the device handle.

19. Due to the soft durometer and elastic nature of the NP Hub O-Ring 25, as the needle 21 and attached needle collet 19 are moved distally, the NP O-Ring 25 deforms allowing the collet to traverse the NP O-ring 25 under applied longitudinal force. Once the needle collet 19 has traversed the NP O-ring 25, the needle 21 with pre-mounted collet 19 are tracked through the catheter sheath 14 to the intended target site. This aspect of the current invention is also illustrated in FIG. 23.

Figure 16:
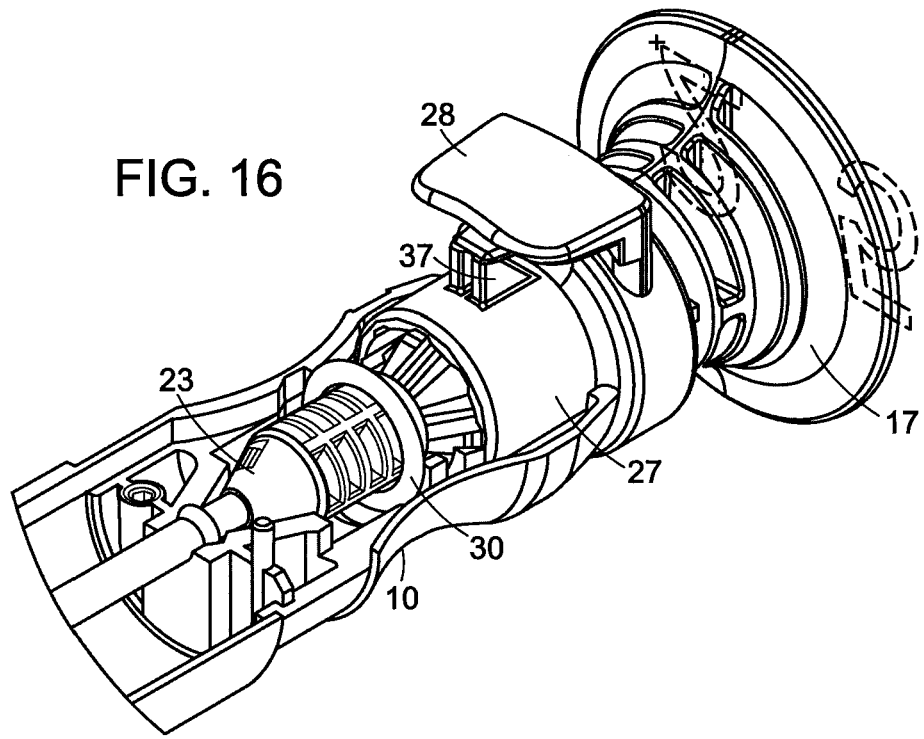
FIG. 16 is a drawing of the intended functionality of the needle protector and aspiration needle assemblies during needle exchange and more specifically, during needle insertion.
Figure 17:
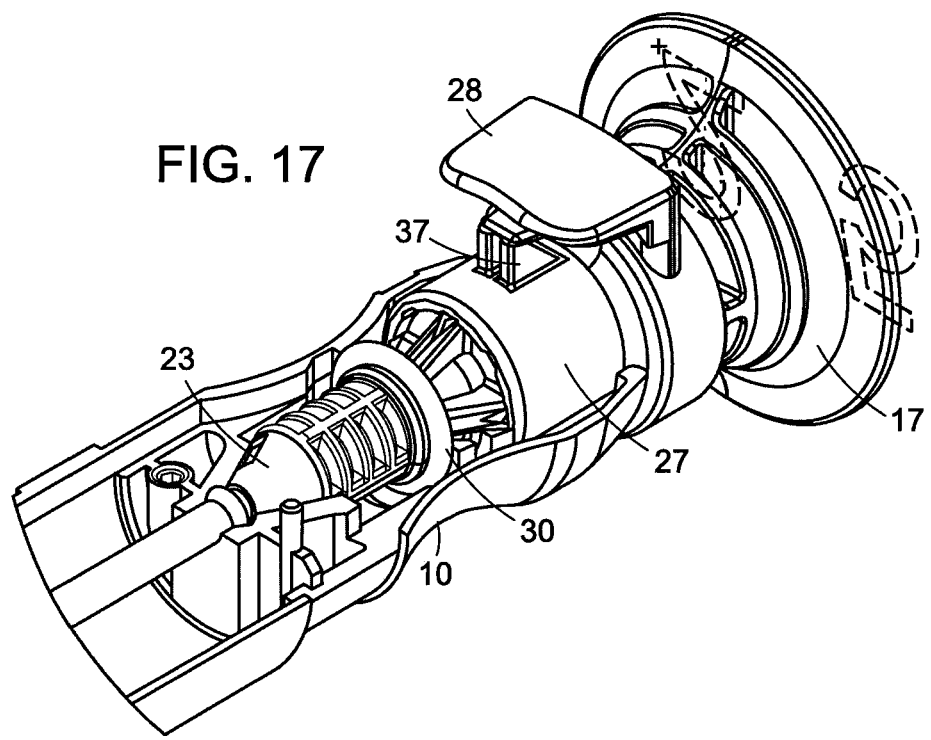
FIG. 17 is a drawing of the intended functionality of the needle protector and aspiration needle assemblies during needle exchange and more specifically, during needle insertion and locking in the device handle.
Figure 18:
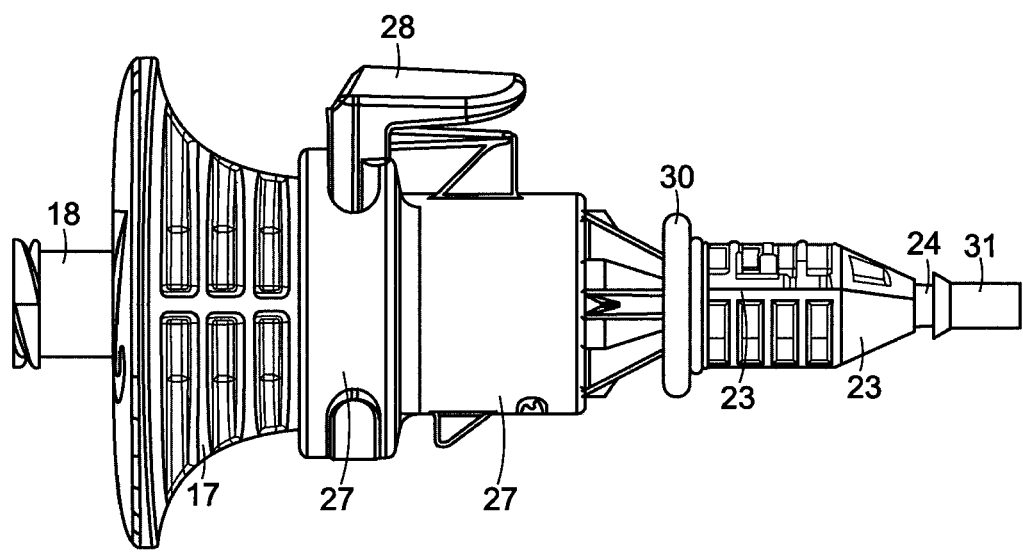
FIG. 18 is a drawing of the locking functionality of the needle protector and aspiration needle sub-assemblies in the hub housing components of the device handle.

FIGS. 16, 17 and 18 illustrate the mechanism by which the aspiration needle sub-assembly 15 is locked into the handle 10 of the delivery system. First, the aspiration needle sub-assembly 15 is pre-mounted with needle protection sub-assembly 9, as previously described. As shown in FIG. 16, at the start of a needle insertion cycle, the aspiration needle/protection assembly is inserted into the proximal handle member 10a of the delivery system handle 10. As the needle/protection assembly is advanced, the needle protector hub 23 contacts the retention collar o-ring 30. Under application of additional force (as illustrated per FIGS. 14 and 15) the needle collet 19 traverses the internal NP Hub O-Ring 25 and advances distally down the catheter sheath 14, as described above. As the needle hub 17 component is advanced into the hub housing component 27 of the proximal handle member 10a, the distal end of the needle hub 17, contacts the proximal end of the NP sub-assembly 9. Continually inserting the needle hub 17, pushes the NP sub-assembly 9 forward so that the NP hub 23 traverses the deformable retention collar o-ring 30 until it comes to rest. At this juncture, the NP hub 23 and sub-assembly 9 are locked in position within the proximal handle member 10a and do not move. Simultaneously, the needle hub 17 deflects the thumb latch component 28. Once the NP sub-assembly 9 has traversed the retention collar o-ring 30 (as shown in FIG. 18), the needle hub 17 is securely locked into the hub housing 27 by traversing an internal land ring 36 on the needle hub component 17, as shown in Detail F of FIG. 19.

FIG. 19 illustrates a sectional view of the aspiration needle locked into the thumb latch 28/hub housing 27 components of the delivery system handle 10. As the needle hub 17 is advanced into the hub housing 27 in the handle, the hub 17 contacts the internal taper of the thumb latch 28 at the thumb latch distal end. This causes the thumb latch 28 distal end to move laterally and also causing the deflectable hinge 28a of the thumb latch 28 (see FIG. 22 also) to deform under plastic deformation, against the hub housing barb 37. Once the needle hub 17 is completely advanced into the hub housing 27, the distal end portion of the thumb latch 28, returns to the home position. The interference between the internal land ring 36 on the needle hub 17 and the thumb latch distal end, ensures that the needle hub 17 will not move backwards.

Figure 22:
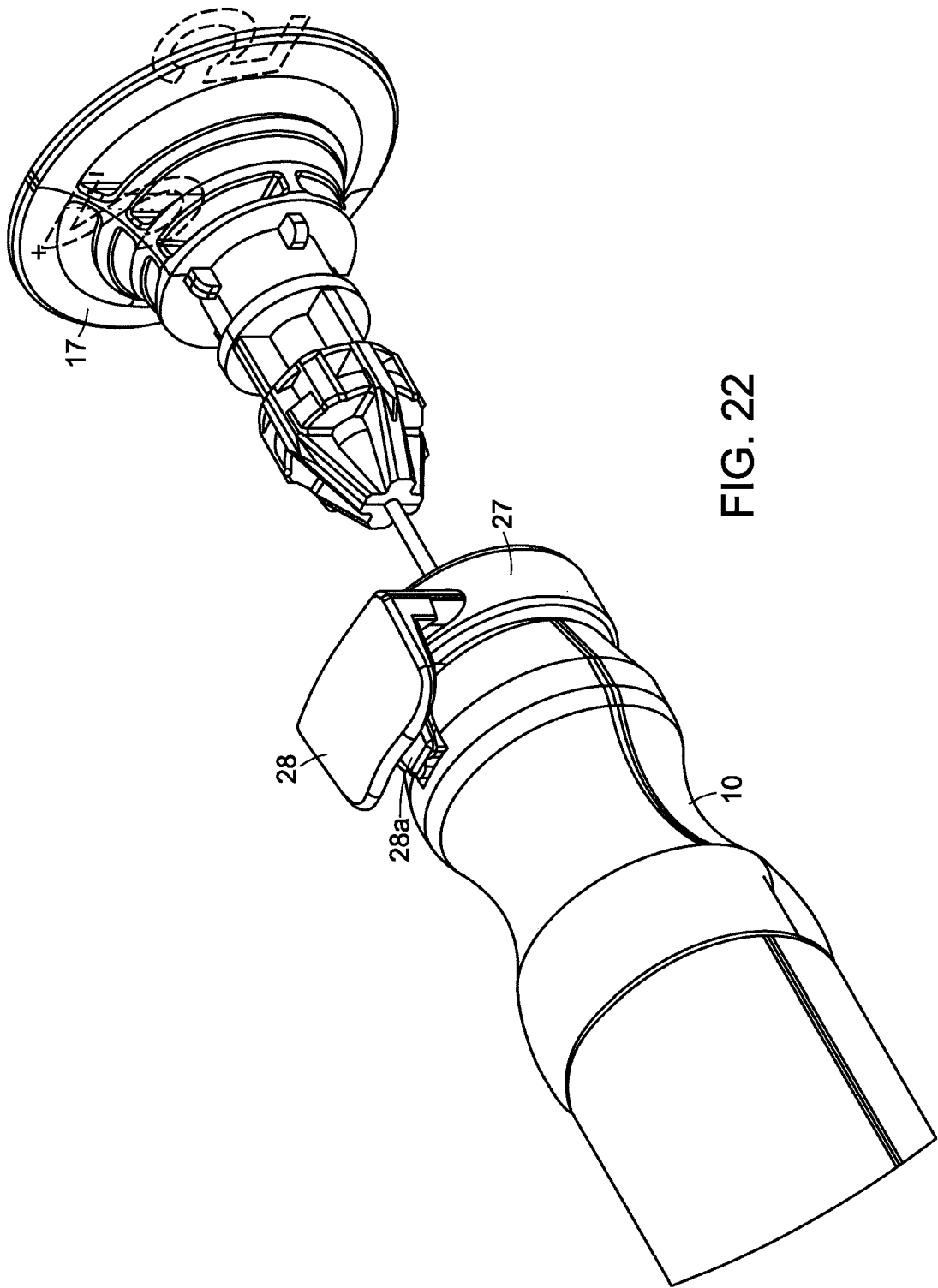
FIG. 22 is a drawing of the intended functionality of the present invention to withdraw the aspiration needle sub-assembly from the delivery system handle during needle exchange.

An intended functionality of thumb latch 28 is to prevent the aspiration needle subassembly 15 from being removed from the proximal handle member 10a without applying force to release thumb latch 28. As shown in FIG. 22, the aspiration needle may be exchanged or withdrawn from the delivery system handle 10 by depressing the thumb latch component 28 and withdrawing the needle hub 17 from the hub housing 27. As the thumb latch 28 is depressed, the deflectable hinge 28a of the thumb latch 28 contacts the hub housing barb 37. The thumb latch 28 moves in a lateral direction. This action clears the interference between the internal needle hub land ring 36 and distal end of the thumb latch component 28. In this way, the aspiration needle can be removed un-impaired from the delivery system handle. Additionally, follow-up samples may be acquired using the same or a virgin aspiration needle sub-assembly.

Figure 20:
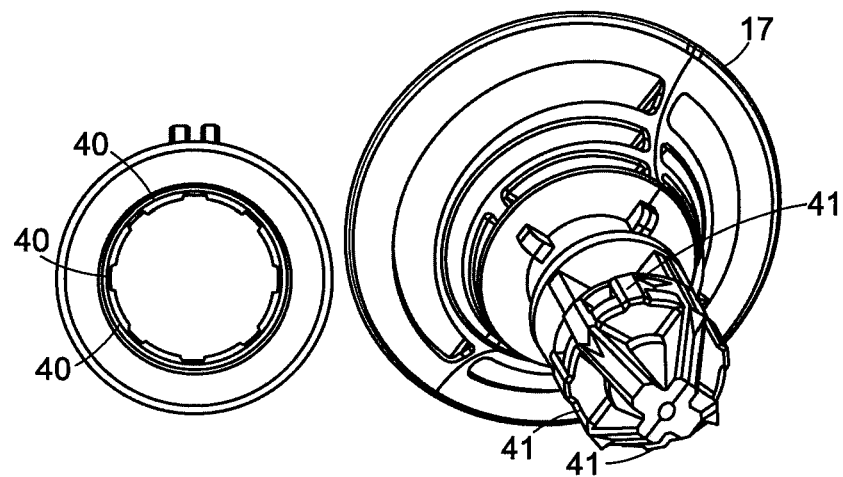
FIG. 20 is a drawing of the hub needle hub and hub housing with interlocking capability to ensure non-rotation.
Figure 21:
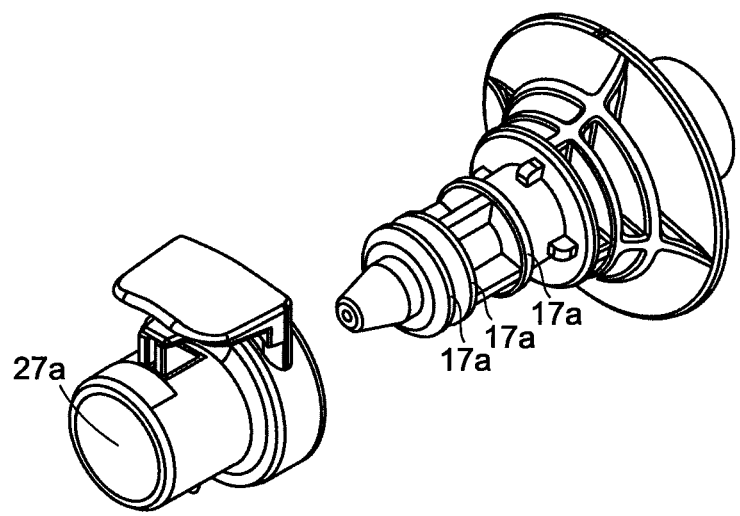
FIG. 21 is an alternate embodiment of the present invention, to facilitate rotation between needle hub and hub housing components.

FIG. 20 illustrates the preferred embodiments of the hub housing 27 and needle hub 17 embodiments of the present invention. In this instance, the hub housing component 27 contains depressed female détentes 40 on the inner diameter of the hub housing 27. These détente features 40 are equispaced around the internal circumference of the hub housing body. It is preferable that the number of détente features be in the range of 2 to 15, but more preferably in the range of 6 to 10. These détente features provide a mechanical lock with corresponding interlocking barb features 41 on the external surface of the needle hub barrel 17. Once the needle hub 17 is securely locked in the hub housing component 27 in the device handle, the interlocking barbs 41 on the needle hub 17 become seated in the détente features 40 of the hub housing. This mechanical lock prevents the needle hub 17 from rotating relative to the needle hub housing 27 and delivery system handle 10, during a typical endoscopic ultrasound procedure. Alternatively, the inner surface of the hub housing component 27 can be a smooth inner surface 27a. Likewise, the external surface of the needle hub 17 is smooth external surface 17a, to allow the needle hub 17 to rotate relative to the needle hub housing 27 and delivery handle system 10 during an endoscopic ultrasound procedures (FIG. 21).

Figure 24:
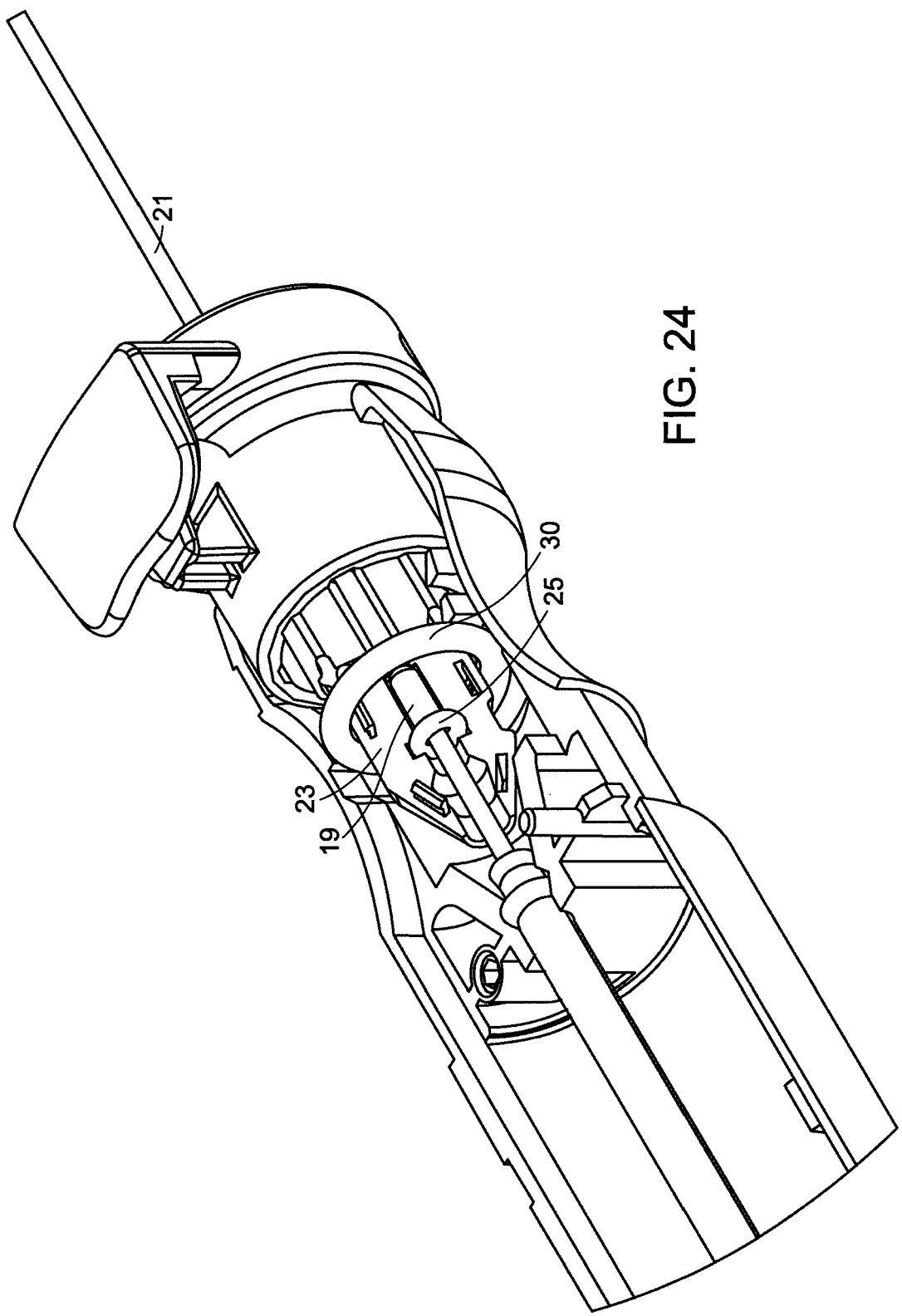
FIG. 24 is a drawing of the intended functionality of the needle collet during needle exchange and more specifically, during needle extraction from the device handle.

During aspiration needle exchange, and more specifically during needle insertion, the needle collet component 19 disengages from the NP Hub O-Ring 25 by traversing the NP Hub O-Ring 25 as explained above. FIGS. 23 and 24 illustrate the engagement of the needle collet 19 with the needle protector sub-assembly 9 upon needle extraction post sample acquisition. As the aspiration needle is continually withdrawn from the delivery system handle 10, the needle collet 19 contacts the NP hub O-ring 25 as shown in FIG. 23. As the aspiration needle is continually withdrawn, the needle collet 19 traverses the NP hub O-ring 25 as shown in FIG. 24. As the needle is further withdrawn, the needle protector hub 23 traverses the retention collar O-ring 30 and the needle can be completely removed from the system, with the needle protector sub-assembly 9 encasing the distal bevel of the needle 35 to prevent inadvertent "needle sticking", as illustrated in FIG. 25 and Detail G.

Figure 25:
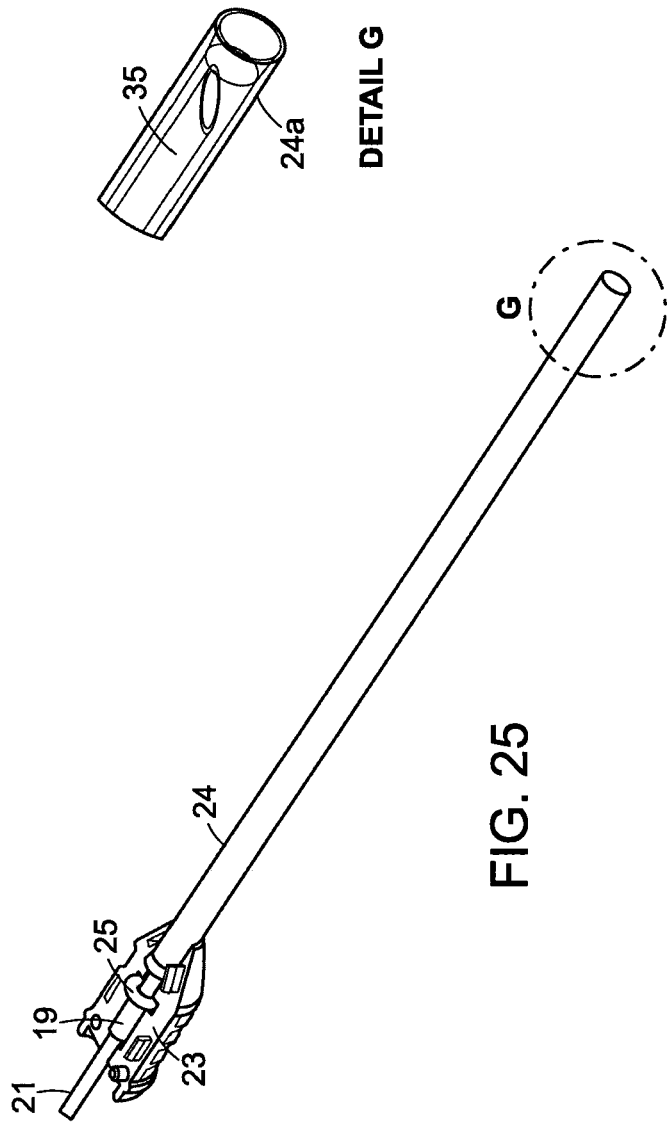
FIG. 25 is a drawing of the needle protector sub-assembly secured to the end of the aspiration needle, and the intended functionality of the needle sheath of the present invention.

In the case of the present invention, the needle protector sheath 24 is internally tapered 24a at the distal end (FIG. 25). It is preferable that length of this internal taper be in the range of 1 mm to 10 mm but more preferably in the range of 3 mm to 6 mm. It is also preferable that the internal taper angle on the distal end of the needle protector sheath be in the range of 2 degrees to 30 degrees, but more preferably in the range of 5 degrees to 15 degrees.

Figure 26:
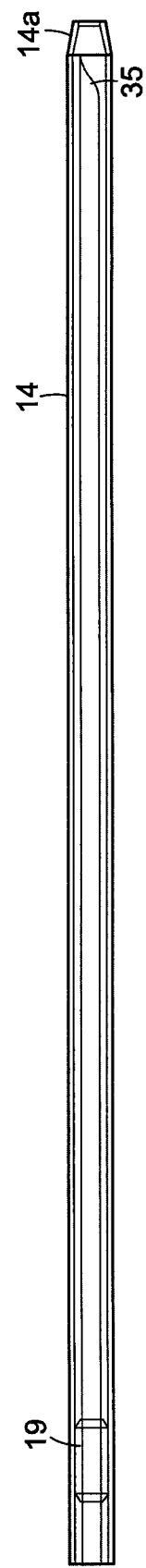
FIG. 26 is a drawing of the distal end of the aspiration needle sub-assembly housed in the catheter sheath of the delivery system of the present invention.
Figure 27:
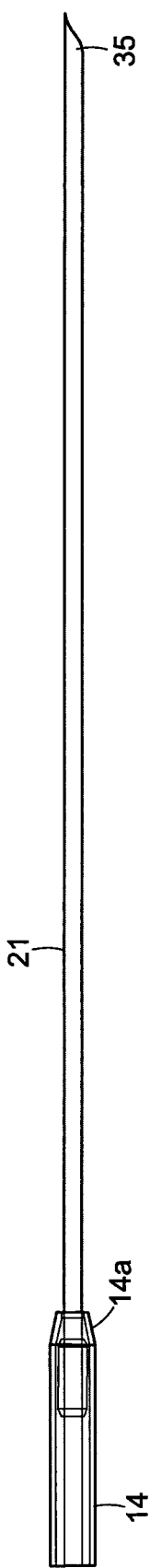
FIG. 27 is a drawing of the distal end of the aspiration needle sub-assembly extending from the catheter sheath of the delivery system of the present invention.

FIG. 26 is an illustration of the distal end 14a of the catheter sheath 14 of the delivery system (not shown) with aspiration needle loaded in the device handle, with the device handle in the fully retracted position. In this instance, the distal end of the needle lies proximal to the distal tapered end 14a of the catheter sheath 14. FIG. 27 illustrates the position of the needle 21 and needle collet 19 relative the catheter sheath 14 when the needle is in it's fully extended position. In the fully extended position, the needle collet 19 remains housed inside catheter sheath 14, proximal to the tapered distal tip.

Figure 29:
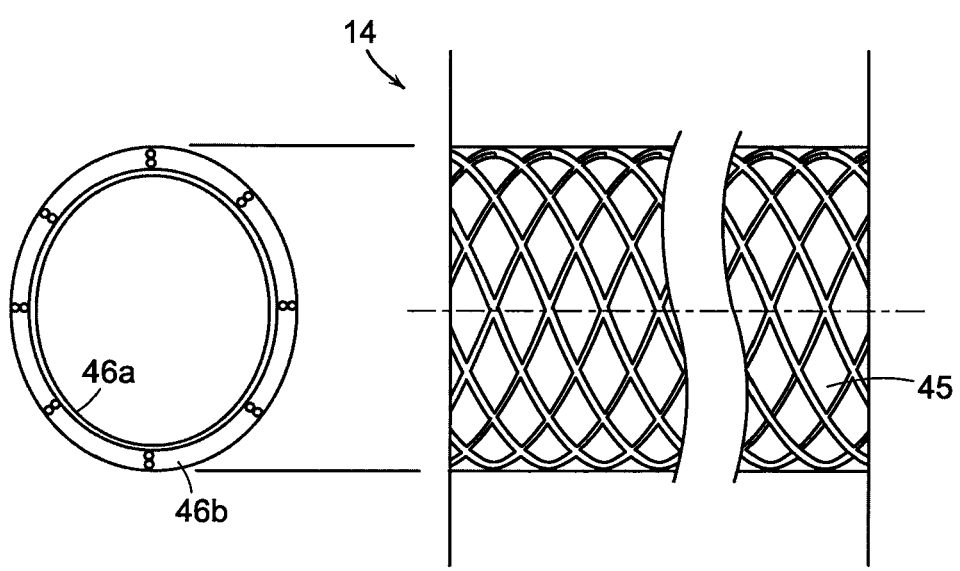
FIG. 29 is a drawing of the construction of the catheter sheath component of the present invention.

In the case of the present invention, the catheter shaft component 14 is manufactured from a thermoplastic polymer such as, but not limited to Polyurethane, Polyamide and derivatives thereof, Ether block amide copolymers, Polyimide, Placental, Polyethylene and derivatives thereof, Polytetrafluoroethylene. The preferred embodiment of the catheter shaft 14 (as shown in FIG. 29) is that the catheter shaft 14 incorporates a helically braided reinforcing structure 45 housed between inner 46a and outer polymer 46b layers, of outer thermoplastic material such as those mentioned above with a lubricious inner liner or core. In the case of the present invention, the helically braided reinforcement 45 is fabricated from stainless steel wire. It is preferable that the diameter of this reinforcing braid wire be in the range of 0.0005 inches to 0.010 inches but more preferably in the range of 0.0015 inches to 0.005 inches It is preferable that the outer diameter of the catheter sheath 14 be in the range of 0.050 inches to 0.140 inches but more preferably in the range of 0.085 inches to 0.0105 inches. It is preferable that the inner diameter of the catheter sheath 14 be in the range of 0.050 inches to 0.120 inches but more preferably in the range of 0.065 inches to 0.085 inches.

In the case of the present invention (and as illustrated in FIGS. 26 and 27), it is preferable that the distal end 14a of the catheter sheath 14 be tapered to reduce both the outer diameter and the internal diameter of the catheter sheath tip. This taper may be imparted to the distal end of the catheter sheath 14 via swaging or thermal heat forming techniques. It is preferable that the inner diameter of the catheter sheath 14 be tapered at the distal end 14a to an internal diameter in the range of 0.020 inches to 0.060 inches but more preferably in the range of 0.040 inches to 0.050 inches.

Figure 28:
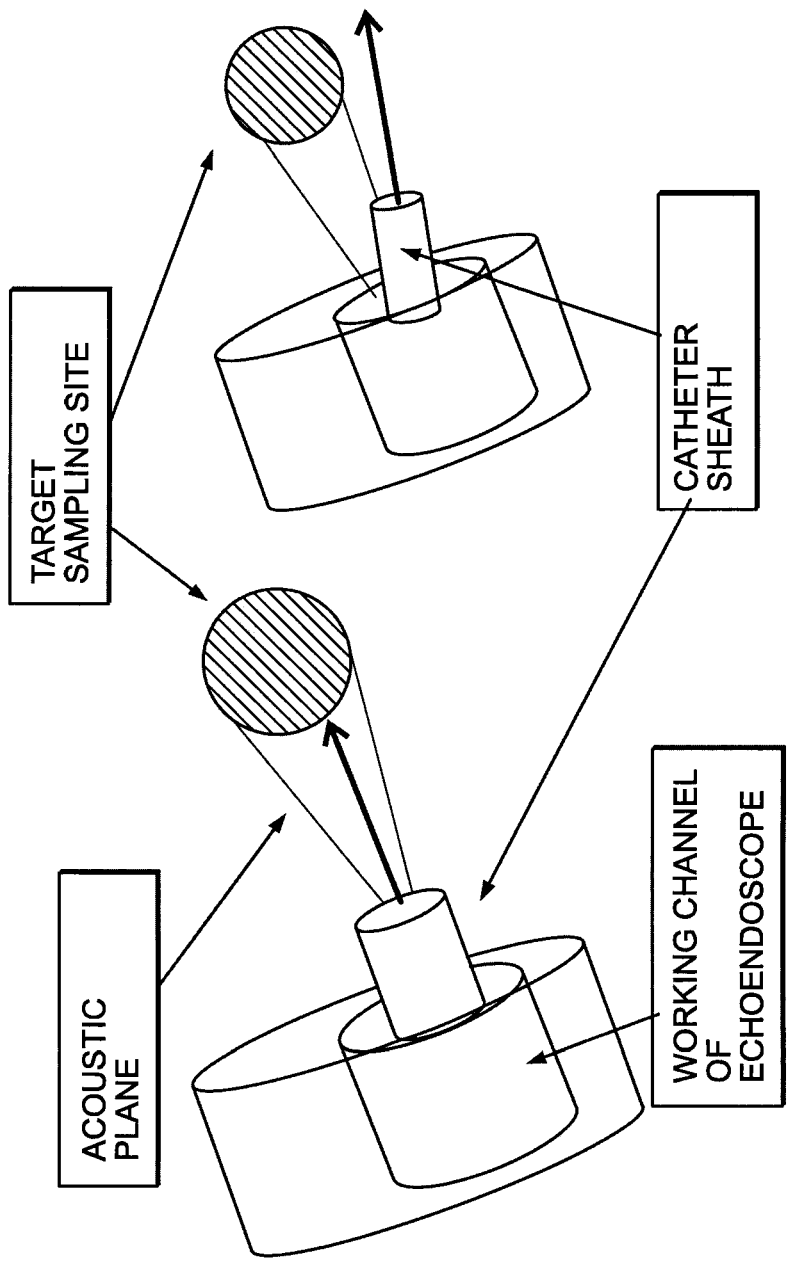
FIG. 28 is a drawing of the intended functionality of the present invention, and more specifically of the intended functionality of the catheter sheath of the present invention.

Referring now to FIG. 28, An aspect of the present invention which provides the clinician with improved procedural performance over prior art devices, concerns the ability of the tapered catheter sheath 14 of the present invention to keep the aspiration needle of the device centered in the working channel conduit of the endoscope. Due to the increased outer diameter of the catheter sheath 14 of the present invention (in the range of 6.5 French to 8 French) compared to that of the prior art (approximately 5 French to 5.4 French), the catheter sheath reduces the annular clearance between the catheter sheath 14 and the inner diameter of the endoscope working channel. By reducing the annular clearance with the working channel of the endoscope, the angle of exit of the catheter sheath 14 of the present invention is co-axial to working channel. This ensures that as the needle exits the distal end of the catheter sheath, the needle will exit the distal end of the catheter in a more "normal" plane relative to the longitudinal axis of the endoscope. The inclusion of an internal taper on the distal end of the catheter sheath, also ensures that the needle exits the catheter in a more "normal" plane than in the case of prior art devices.

Certain embodiments according to the invention have been disclosed. These embodiments are illustrative of, and not limiting on, the invention. Other embodiments, as well as various modifications and combinations of the disclosed embodiments, are possible and within the scope of the disclosure.

What is claimed is:

1. A device for needle biopsy comprising:
an adjustable delivery handle system, at least a portion of the delivery handle system comprising an inner lumen configured to interchangeably receive a needle subassembly;
a proximal handle member disposed at a proximal end of the delivery handle system; and
a needle subassembly removably disposed within the inner lumen and comprising an interchangeable needle having a protruded portion at a distal end portion of the interchangeable needle, wherein the needle subassembly further comprises a needle protector subassembly having an internal protruded portion that is configured to engage with the protruded portion of the interchangeable needle and lock onto the protruded portion at the distal end portion of the interchangeable needle in response to withdrawing the needle subassembly from the delivery handle system such that the distal end portion of the interchangeable needle transitions from an unshielded configuration to a shielded configuration within the proximal handle member upon engaging the internal protruded portion of the needle protector subassembly with the protruded portion at the distal end portion of the interchangeable needle within the proximal handle member, wherein the needle protector subassembly and the interchangeable needle are reinsertable into the delivery handle system,
wherein the protruded portion of the interchangeable needle is configured to traverse the internal protruded portion of the needle protector subassembly in response to applying a longitudinal force to the interchangeable needle when the interchangeable needle is reinserted into the delivery handle system such that the internal protruded portion transitions from a deformed state to an undeformed state upon applying the longitudinal the force, thereby unlocking the protruded portion from the internal protruded portion within the proximal handle member in response to reinserting the needle subassembly into the delivery handle system.

2. The device of claim 1, wherein the interchangeable needle comprises a distal tip having four distinct angular bevel grinds.

3. The device of claim 2, wherein the four distinct angular bevel grinds of the distal tip of the interchangeable needle comprise a primary angle relative to a needle shaft, a secondary angle relative to the needle shaft, and a back-cut angle relative to the secondary angle for providing a smooth needle passage during needle insertion and withdrawal during a biopsy procedure.

4. The device of claim 3, wherein the distal tip of the interchangeable needle comprises an enhanced echogenicity or acoustic reflection region.

5. The device of claim 1, wherein the delivery handle system has an adjustable length, a longitudinal axis defining a lumen extending therethrough, and comprising the proximal handle member, a middle handle member and a distal handle member, the proximal handle member being slideably disposed over at least a portion of the middle handle member, the middle handle member being slideably disposed over at least a portion of the distal handle member, the proximal handle member comprising an inner hub housing component comprising an internally cylindrical shape configured to interchangeably receive the needle subassembly configured for inserting into and withdrawing from the proximal handle member.

6. The device of claim 5, wherein the interchangeable needle comprises:
a proximal end portion and the distal end portion;
a needle luer coupled to the proximal end portion of the needle; and
a needle hub coupled to the proximal end portion of the needle, the needle hub configured for coupling with the inner hub housing component of the proximal handle member.

7. The device of claim 6, wherein the needle protector subassembly comprises:

a needle protection hub having a lumen extending therethrough configured for receiving the distal end portion of the needle;

the internal protruded portion comprises a deformable O-ring axially disposed within the lumen of the needle protection hub; and a tubular sheath defining a lumen extending from a distal end of the needle protection hub, the lumen of the tubular sheath in communication with the lumen of the needle protection hub for receiving the needle when inserted into the needle protection hub.

8. The device of claim 7, wherein the protruded portion at the distal end portion of the interchangeable needle comprises a collet surrounding the distal end portion of the needle, the collet comprising a diameter larger than the diameter of the deformable O-ring of the needle protection hub such that the collet traverses the deformable O-ring when the needle is inserted into or withdrawn from the lumen of the needle protection hub, thereby locking the needle protector subassembly onto the distal end portion of the needle during insertion and withdrawal of the needle subassembly from the delivery handle system.

9. The device of claim 8, wherein the collet is chamfered at a proximal end and a distal end of the collet to provide a smooth interface with the needle protector subassembly during needle exchange.

10. The device of claim 7, wherein the proximal handle member further comprises an inner retention collar disposed at a distal end of the inner hub housing component, the inner retention collar configured to receive the needle protection hub coupled to the needle, at least a portion of the inner retention collar being recessed, and a deformable O-ring component disposed within a recessed portion for securing the needle protection hub within the inner retention collar upon insertion of the needle subassembly into the proximal handle member.

11. The device of claim 10, wherein the O-ring component of the inner retention collar has a diameter smaller than a diameter of the needle protection hub, such that the needle protection hub traverses the deformable O-ring when the needle subassembly is inserted into or withdrawn from the proximal handle member thereby locking the needle protector subassembly onto the proximal handle member during insertion and withdrawal of the needle subassembly from delivery handle system.

12. The device of claim 7, wherein the proximal handle member further comprises a locking mechanism for releasably locking the needle hub within the inner hub housing component of the proximal handle member.

13. The device of claim 12, wherein the locking mechanism comprises a depressible latch component securely coupled to the proximal handle member, the latch component comprising a deflectable hinge coupled to a barb component, the barb component coupled to the inner hub housing component, disposed within an interior portion of the proximal handle member.

14. The device of claim 13, wherein the needle hub of the needle subassembly further comprises an internal land ring for interacting with the deflectable hinge and barb component of the locking mechanism, whereby the internal land ring traverses the deflectable hinge of the latch component when the needle subassembly is inserted into the lumen of the proximal handle member, thereby causing the deflectable hinge to deflect against the barb component during insertion, the deflectable hinge returning to a home position once the internal land ring has cleared the deflectable hinge to prevent the needle hub from moving backwards, and whereby the needle subassembly is released from the inner hub housing component of the proximal handle member by depressing the latch component to cause the deflectable hinge to deflect against the barb component to allow the internal land ring to clear the deflectable hinge and barb.

15. The device of claim 7, wherein the inner hub housing component comprises a plurality of depressions spaced around an internal circumference of the inner hub housing component and the needle hub comprises a plurality of protrusions, the plurality of depressions configured to receive the plurality of protrusions to prevent the needle hub from rotating relative to the inner hub housing component.

16. The device of claim 7, wherein the inner hub housing component comprises a smooth internal circumference and the needle hub comprises a smooth outer surface to allow the needle hub rotate relative to the inner hub housing component.

17. The device of claim 5, wherein the inner lumen, extending through the adjustable delivery handle system, comprises:

an inner hypotube component at least partially disposed within the proximal handle member;

an outer hypotube component disposed at least partially within the middle handle member, the inner hypotube component being coupled to the outer hypotube component and configured to longitudinally slide within the outer hypotube component when the proximal handle member is distally advanced or proximally retracted over the middle handle member; and a tubular catheter sheath coupled to a distal end of the outer hypotube component, wherein the inner hypotube component, outer hypotube component, and tubular catheter sheath are in constant communication with each other.

18. The device of claim 17, further comprising an inner handle member disposed within an inner portion of the middle handle member, the inner handle member coupled to a proximal portion of the tubular catheter sheath and a distal portion of the outer hypotube component, such that the tubular catheter sheath is distally extended into the distal handle member when the middle handle member is distally advanced over the distal handle member.

19. The device of claim 17, wherein the tubular catheter sheath comprises an outer diameter ranging from 0.05 inches to 0.140 inches, and an inner diameter ranging from 0.05 inches to 0.120 inches.

20. The device of claim 17, wherein the tubular catheter sheath comprises a tapered distal tip comprising an outer diameter and an inner diameter, wherein the outer diameter and the inner diameter of the tapered distal tip are smaller than an outer diameter and an inner diameter of the tubular catheter sheath, respectively.

* * * * *